(12) United States Patent
Gogolak

(10) Patent No.: US 6,789,091 B2
(45) Date of Patent: Sep. 7, 2004

(54) METHOD AND SYSTEM FOR WEB-BASED ANALYSIS OF DRUG ADVERSE EFFECTS

(76) Inventor: Victor Gogolak, 934 Douglass Dr., McLean, VA (US) 22101

( * ) Notice: Subject to any disclaimer, the term of this patent is extended or adjusted under 35 U.S.C. 154(b) by 123 days.

(21) Appl. No.: 09/681,583

(22) Filed: May 2, 2001

(65) Prior Publication Data

US 2002/0165845 A1 Nov. 7, 2002

(51) Int. Cl.⁷ .............................. G06F 17/00; G06F 7/00
(52) U.S. Cl. ........................................ 707/104.1; 707/1
(58) Field of Search ......................... 707/3, 102, 104.1, 707/9–10; 705/2–3

(56) References Cited

U.S. PATENT DOCUMENTS

| | | |
|---|---|---|
| 5,299,121 A | 3/1994 | Brill et al. ............. 364/413.01 |
| 5,337,919 A | 8/1994 | Spaulding et al. ............. 221/2 |
| 5,371,807 A | 12/1994 | Register et al. ............... 382/14 |
| 5,495,604 A | 2/1996 | Harding et al. ............. 395/600 |
| 5,502,576 A | 3/1996 | Ramsay et al. ............. 358/444 |
| 5,583,758 A | 12/1996 | McIlroy et al. ............. 395/202 |
| 5,592,668 A | 1/1997 | Harding et al. ............. 395/602 |
| 5,594,637 A | 1/1997 | Eisenberg et al. .......... 395/202 |
| 5,634,053 A | 5/1997 | Noble et al. ................. 395/604 |
| 5,642,731 A | 7/1997 | Kehr .......................... 128/630 |
| 5,664,109 A | 9/1997 | Johnson et al. ................. 705/2 |
| 5,692,171 A | 11/1997 | Andres ........................ 395/601 |
| 5,737,539 A | 4/1998 | Edelson et al. ............. 395/203 |
| 5,758,095 A | 5/1998 | Albaum et al. ............. 395/202 |
| 5,804,803 A | 9/1998 | Cragun et al. ............. 235/375 |
| 5,833,599 A | 11/1998 | Schrier et al. ............. 600/300 |
| 5,845,255 A | 12/1998 | Mayaud .......................... 705/3 |
| 5,860,917 A | 1/1999 | Comanor et al. ........... 600/300 |
| 5,864,789 A | 1/1999 | Lieberman et al. ............ 704/9 |
| 5,911,132 A | 6/1999 | Sloane ........................... 705/3 |
| 5,924,074 A | 7/1999 | Evans ............................ 705/3 |
| 6,000,828 A | 12/1999 | Leet ........................... 364/401 |
| 6,014,631 A | 1/2000 | Teagarden et al. .............. 705/3 |
| 6,067,524 A | 5/2000 | Byerly et al. ................... 705/3 |
| 6,076,083 A | 6/2000 | Baker .......................... 706/52 |
| 6,076,088 A | 6/2000 | Paik et al. ...................... 707/5 |
| 6,082,776 A | 7/2000 | Feinberg ....................... 283/72 |
| 6,108,635 A | 8/2000 | Herren et al. ................... 705/2 |
| 6,112,182 A * | 8/2000 | Akers et al. .................... 705/2 |
| 6,120,443 A | 9/2000 | Cohen-Laroque ........... 600/300 |
| 6,137,911 A | 10/2000 | Zhilyaev ..................... 382/225 |
| 6,151,581 A | 11/2000 | Kraftson et al. ............... 705/3 |
| 6,219,674 B1 | 4/2001 | Classen ...................... 707/104 |
| 6,226,564 B1 | 5/2001 | Stuart ......................... 700/231 |
| 6,263,329 B1 | 7/2001 | Evans ............................ 707/3 |
| 6,317,719 B1 * | 11/2001 | Schrier et al. ................. 705/2 |
| 6,542,902 B2 * | 4/2003 | Dulong et al. ........... 707/104.1 |

OTHER PUBLICATIONS

Kapp, Web–Based Medication Management System, Jan. 24, 2002, US Patent Application Publication, Pub. No.: US 2002/0010595.*

(List continued on next page.)

Primary Examiner—Greta Robinson
Assistant Examiner—Susan F. Rayyan
(74) Attorney, Agent, or Firm—Shaw Pittman LLP

(57) ABSTRACT

A computer-implemented method for accessing and analyzing the adverse effects resulting from the use of at least one drug of interest. The method includes storing data regarding the risks of adverse effects from the use of at least one drug of interest in one or more servers linked to the Internet. This data is updated with additional information pertinent to the risks of adverse effects from the use of the at least one drug of interest. A remote user is permitted to access the data through the World Wide Web upon proper authentication. The remote user is permitted to identify the at least one drug of interest and select data stored in one or more servers relevant to the safety of using the at least one drug of interest. The remote user is then permitted to analyze safety issues resulting from use of the at least one drug of interest and to display the requested data and any resulting analysis.

16 Claims, 18 Drawing Sheets

OTHER PUBLICATIONS

Multum Trusted Health Information [online], [retrieved on Aug. 22, 2002], 1 p., Retrieved from the Internet: http://www.multum.com.

Epocrates [online], Copyright 2002 [retrieved on Aug. 22, 2002], 1 p., Retrieved from the Internet: http://www.epocrates.com.

PDR.net [online], Copyright 2002 [retrieved on Aug. 22, 2002], 1 p., Retrieved from the Internet: http//www.pdr.net/HomePage_template.jsp.

"VAERS Data: Guide to Interpreting Case Report Information Obtained From the Vaccine Adverse Event Reporting System (VAERS)" [online], retrieved on Jun. 11, 2002, 2 pp., Retrieved from the Internet: http://www.vaers.org/info.

Szarfman, Ana, M.D., Ph.D., "Application of Screening Algorithms and Computer Systems to Efficiently Signal Combinations of Drugs and Events in FDA's Spontaneous Reports" [online], Oct. 22, 2001, 2 pp., Retrieved from the Internet: http://apha.confex.com/apha/129.am/techprogram/paper_32272.

"Vaccine Adverse Event Reporting System (VAERS)" [online], U.S. Department of Health and Human Services, Jul., 2001 [retrieved Jul., 2001], 12 pp., Retrieved from the Internet: http://www.vaers.org/search/README.

Andrews, Michelle, "Prescription for Disaster," *Smart-Money*, pp. 124–129, May, 2001.

Mootrey, Gina, et al., "Chapter 18: Surveillance for Adverse Events Following Vaccination," *VPD Surveillance Manual*, 20 pp., 1999.

Szarfman, Ana, M.D., Ph.D., "New Methods for Signal Detection," *Proceedings of the 15th International Conference on Pharmacoepidemiology*, 56 pp., Aug. 28, 1999.

DuMouchel, William, "Bayesian Data Mining in Large Frequency Tables, with an Application to the FDA Spontaneous Reporting System," *The American Statistician*, vol. 53, No. 3., 31 pp., Apr., 1999.

"The Totally Unauthorized, Completely Repudiated, Bootlegged, Unsupported, Undocumented, Insider's Post–Pre–Alpha Guide to Multum's Lexicon," Multum Information Services, Inc., pp. 1–49, Copyright 1997–1999, Apr. 12, 1999 (Rev. 3.d).

"Post–Marketing Surveillance for Adverse Events After Vaccination: The National Vaccine Adverse Event Reporting System (VAERS)," *Medwatch*, 12 pp., Nov., 1998.

Lipschutz, Seymour, Ph.D., "Theory and Problems of Linear Algebra," Schaum's Outline Series, McGraw–Hill Book Company Company, 5 pp., 1968.

Anderson, T. W., "A Bibliography of Multivariate Statistical Analysis," Oliver & Boyd, Edinburgh, 3 pp., 1972.

Darlington, Richard B., "Regression and Linear Models," McGraw–Hill Publishing Company, 15 pp., 1990.

Press, James S. and Wilson, Sandra, "Choosing Between Logistic Regression and Discriminant Analysis," *Journal of the American Statistical Association*, vol. 73, pp. 699–705, Dec., 1978.

Kosko, Bart, "Neural Networks and Fuzzy Systems—A Dynamical Systems Approach to Machine Intelligence," Prentice Hall, Englewood Cliffs, NJ, 11 pp.,1992.

International Search Report for Application No. PCT/US02/13666, dated Jul. 16, 2002 (mailing date).

International Search Report for Application No. PCT/US02/13662, dated Jul. 15, 2002 (mailing date).

* cited by examiner

HOME > DRUG SELECTOR
SELECTOR/PROFILER:               DATA SOURCE: FDA SRS/AERS COMBINED DATA
GENERIC NAME: 501    TRADE NAMES:         THERAPEUTIC CATEGORIES:
[          ]         [          ]         ACE INHIBITORS ▶
[SEARCH]             [SEARCH]             [SEARCH]  502

FILTERING:
SAVED FILTER: [SELECT ▶]  [VIEW]  [APPLY]

22 DRUGS IN CATEGORY: ACE INHIBITORS

| GENERIC NAME | TRADE NAMES | THERAPEUTIC CATEGORIES | PEDIGREE |
|---|---|---|---|
| AMILORIDE HYDROCHLORIDE | AMILORIDE ▶ | ACE INHIBITORS ▶ | ? |
| AMLODIPINE BESYLATE | AMLODIPINE ▶ | ACE INHIBITORS ▶ | ? |
| BENAZEPRIL HYDROCHLORIDE | BENAZEPRIL ▶ | ACE INHIBITORS ▶ | ? |
| CANDESARTAN CILEXETIL | ATACAND ▶ | ACE INHIBITORS ▶ | ? |
| CAPTOPRIL | ACE-HEMMER ▶ | ACE INHIBITORS ▶ | ? |
| ENALAPRIL MALEATE | ACETENSIL ▶ | ACE INHIBITORS | ? |

*FIG. 5*

| DATA PEDIGREE 600 | 601 | 602 | 603 | 604 | 605 | 606 | 607 |
|---|---|---|---|---|---|---|---|
| MAP TO / VERBATIM | SOURCE | INCIDENTS | CASE COUNT | QEDRx PROCESSING | CROSS-REFERENCE | FIRST/LAST REPORTED REACTIONS | |
| PROZAC / PROZAC | SRS | 47953 | 47937 | | ORANGE BOOK | APR 27 1969/DEC 2 1997 |
| PROZAC / PROZAC | AERS | 3378 | 3308 | S | ORANGE BOOK | NOV 1 1997/JUN 29 1999 |
| FLUOXETINE / FLUOXETINE HYDROCHLORIDE | SRS | 2204 | 2203 | | NDCD TRADENAME | JAN 1 1979/OCT 14 1997 |
| FLUOXETINE / FLUOXETINE | AERS | 574 | 571 | S | ORANGE BOOK | NOV 1 1997/JUN 18 1999 |
| FLUOXETINE / PROZAC (FLUOXETINE HYDROCHLORIDE) | AERS | 379 | 378 | | ORANGE BOOK | NOV 1 1997/JUN 12 1999 |
| PROZAC / PROZAC (FLUOXETINE) | AERS | 140 | 140 | S | ORANGE BOOK | NOV 7 1997/APR 24 1999 |
| FLUOXETINE / FLUOXETINE HYDROCHLORIDE | AERS | 122 | 122 | | M | ORANGE BOOK | NOV 14 1997/JUN 27 1999 |
| FLUOXETINE / FLUOXETINE (FLUOXETINE HYDROCHLORIDE) | AERS | 65 | 65 | | M | ORANGE BOOK | MAR 1 1998/JUN 24 1999 |
| FLUOXETINE / FLUOXETINE HCL | AERS | 34 | 34 | | M | ORANGE BOOK | NOV 1 1997/NOV 1 1998 |
| PROZAC / PROZAC (FLUOXETINE HCL) | AERS | 20 | 20 | | M | ORANGE BOOK | NOV 1 1997/MAR 12 1999 |
| PROZAC / PROZAC (FLUOXETINE HYDROCHLORIDE) | AERS | 17 | 17 | | M | ORANGE BOOK | |
| FLUOXETINE / FLUOXETINE (FLUOXETINE HYDROCHLORIDE) | AERS | 15 | 15 | | M | ORANGE BOOK | NOV 15 1997/JUN 6 1999 |

CONCOMITANT DRUGS — 801 — 802 FILTER...

| TOP 10 DRUGS | SUSPECT S | SUSPECT NS | NON-SUSPECT S | NON-SUSPECT NS | TOTAL | % |
|---|---|---|---|---|---|---|
| HYDROCHLOROTHIAZIDE | 9 | 36 | 0 | 0 | 45 | 10.79% |
| ASPIRIN | 2 | 38 | 0 | 5 | 45 | 10.79% |
| FUROSEMIDE | 2 | 32 | 0 | 1 | 35 | 8.39% |
| DIGOXIN | 0 | 30 | 0 | 0 | 30 | 7.19% |
| AMLODIPINE BESYLATE | 0 | 24 | 4 | 0 | 28 | 6.71% |
| ENALAPRIL MALEATE | 4 | 15 | 0 | 5 | 24 | 5.76% |
| VERAPAMIL HYDROCHLORIDE | 11 | 10 | 0 | 2 | 23 | 5.52% |
| ESTROGENS CONJUGATED | 0 | 23 | 0 | 0 | 23 | 5.52% |
| METOPROLOL SUCCINATE | 8 | 11 | 0 | 3 | 22 | 5.28% |
| METOPROLOL TARTRATE | 0 | 15 | 0 | 7 | 22 | 5.28% |

| SUSPECT TOTAL | NON-SUSPECT TOTAL | TOTAL |
|---|---|---|
| 172 | 1141 | 1313 |

MORE DETAILS...

FIG. 9

DEMOGRAPHICS — 901 — FILTER...

| AGE GROUP | MALE | FEMALE | UNKNOWN | TOTAL | % |
|---|---|---|---|---|---|
| >75 | 18 | 73 | 0 | 91 | 21.82% |
| 51-75 | 89 | 123 | 1 | 213 | 51.08% |
| 31-50 | 30 | 16 | 0 | 46 | 11.03% |
| 16-30 | 2 | 1 | 0 | 3 | 0.72% |
| <16 | 0 | 0 | 0 | 0 | 0.00% |
| UNKNOWN | 11 | 30 | 23 | 64 | 15.35% |
| TOTAL | 150 | 243 | 24 | 417 | |
| % | 35.97% | 58.27% | 5.76% | | |

MORE DETAILS...

| TIMEFRAME | COUNT | % |
|---|---|---|
| 1990-1999 | 446 | 100.00% |
| TOTAL REPORT DATES | | |
| | 446 | |

REPORT DATES (1000), COUNT (1001), FILTER... (1002)

MORE DETAILS...

FIG. 10

| OUTCOME | COUNT | % |
|---|---|---|
| DEATH | 36 | 7.19% |
| DISABILITY | 18 | 3.59% |
| HOSPITALIZATION - INITIAL OR PROLONGED | 231 | 46.11% |
| LIFE-THREATENING | 46 | 9.18% |
| OTHER | 168 | 33.53% |
| REQUIRED INTERVENTION TO PREVENT PERMANENT IMPAIRMENT/DAMAGE | 2 | 0.40% |
| TOTAL SERIOUS OUTCOMES | TOTAL NON-SERIOUS OUTCOMES | TOTAL OUTCOMES |
| 333 | 168 | 501 |

OUTCOMES (1100), COUNT (1101), (1102), FILTER...

MORE DETAILS...

BELOW ARE THE TOP 200 CORRELATED TERMS FOR YOUR ANALYSIS ON CANDESARTAN CILEXETIL (TASK 95) VIEW WITH IMAGE VIEW

| [RANK] | [SCORE] | [TERM 1] | [CATEGORY 1] | [TERM 2] | [CATEGORY 2] |
|---|---|---|---|---|---|
| 1 | 7706 | FEMALE | SEX | CANDESARTAN CILEXETIL | TARGET DRUG |
| 2 | 7661 | RENAL FUNCTION ANALYSES | OTHER REACTION | RENAL FAILURE AND IMPAIRMENT | OTHER REACTION |
| 3 | 7244 | PARALYSIS (EXC CONGENITAL AND CRANIAL NERVE) | OTHER REACTION | CENTRAL NERVOUS SYSTEM HAEMORRHAGES AND CEREBROVASCULAR ACCIDENTS | OTHER REACTION |
| 4 | 6901 | HOS | OUTCOME | CANDESARTAN CILEXETIL | TARGET DRUG |
| 5 | 6888 | TRIAMTERENE | OTHER DRUG | DICLOFENAC SODIUM | OTHER DRUG |
| 6 | 6286 | OTH | OUTCOME | CANDESARTAN CILEXETIL | TARGET DRUG |
| 7 | 5868 | SEX NOT SPECIFIED | SEX | AGE NOT SPECIFIED | AGE |
| 8 | 5773 | VERAPAMIL | OTHER DRUG | TRIAMTERENE | OTHER DRUG |
| 9 | 5765 | HOS | OUTCOME | FEMALE | SEX |
| 10 | 5753 | MALE | SEX | CANDESARTAN CILEXETIL | TARGET DRUG |

*FIG. 13*

CORRELATION DETAILS
ANALYZED DRUG: CANDESARTAN CILEXETIL
CASES FOR TERM PAIR: RENAL FUNCTION ANALYSES [OTHER REACTION]/RENAL AND IMPAIRMENT[OTHER REACTION]
CASES 1 TO 18 OF 18 CASES

| | CASE ID | SEX | MANUFACTURER CONTROL CODE | FDA REPORT RECEIPT DATE | AGE | DRUGS | REACTIONS | SERIOUS |
|---|---|---|---|---|---|---|---|---|
| 1 | 3263641 | F | 19990300088 | 1999-06-17 | 74 | ATACAND | BLOOD CREATININE INCREASED; DIALYSIS NOS; RENAL FAILURE AGGRAVATED | N |
| 2 | 3198047 | F | 19990200143 | 1999-03-12 | 57 | ACURETIC, ATORVASTATIN, ATACAND, CEFIXIME, NITRO-DUR, TERBASMIN EXPECTORANTE | BLOOD CREATININE INCREASED; BLOOD UREA INCREASED; HYPOTENSION NOS; RENAL FAILURE ACUTE | Y |
| 3 | 3171644 | F | 19981100002 | 1999-01-17 | 69 | XANAX, ACETYLSALICYLIC ACID, WELLBUTRIN, ATACAND, ARTHROTEC, DIGOXIN, LEVAQUIN, CLARITIN, ANTIVERT, PYRIDIUM, ZOLOFT, DYAZIDE, VERAPAMIL-SLOW RELEASE, AMBIEN | ABDOMINAL PAIN NOS; BLOOD CREATININE INCREASED; BLOOD UREA INCREASED; CORONARY ARTERY DISEASE NOS; HAEMOPTYSIS; HEART RATE INCREASED; HYPERTENSION AGGRAVATED; RENAL FAILURE ACUTE | N |
| 4 | 3270258 | F | 19990400499 | 1999-06-26 | 75 | ATACAND, HYDROCHLOROTHIAZIDE | ATRIOVENTRICULAR BLOCK SECOND DEGREE; BLOOD CREATININE INCREASED; BLOOD PRESSURE DECREASED; ELECTROCARDIOGRAM ST SEGMENT DEPRESSION; ELECTROCARDIOGRAM U WAVE APPEARANCE; ELECTROLYTE IMBALANCE; HYPOCHLOREEMIA; HYPOKALEEMIA; HYPONATRAEMIA; LOSS OF CONSCIOUSNESS NEC; RENAL IMPAIRMENT NOS; SYNCOPA | N |

FIG. 14

CORRELATION DETAILS
ANALYZED DRUG: CANDESARTAN CILEXETIL
CASE FOR TERM PAIR: RENAL FUNCTION ANALYSES [OTHER REACTION]/RENAL FAILURE AND IMPAIRMENT [OTHER REACTION]

| | | | | |
|---|---|---|---|---|
| CASE ID: | 3198047 | | | |
| SEX: | F | | | |
| AGE: | 57.0 YEARS 0.0 MONTHS | | | |
| REACTIONS: | AS REPORTED | PREFERRED TERM | HIGH LEVEL TERM | HIGH LEVEL GROUP TERM | SYSTEM ORGAN CLASS |
| | BLOOD CREATININE INCREASED | BLOOD CREATININE INCREASED | RENAL FUNCTION ANALYSES | INVESTIGATIONS AND URINALYSIS | INVESTIGATIONS |
| | BLOOD UREA INCREASED | BLOOD UREA INCREASED | RENAL FUNCTION ANALYSES | INVESTIGATIONS AND URINALYSIS | INVESTIGATIONS |
| | HYPOTENSION NOS | HYPOTENSION NOS | HYPOTENSION | BLOOD PRESSURE DISORDERS AND DECREASED AND NON-SPECIFIC SHOCK | VASCULAR DISORDERS |
| | RENAL FAILURE ACUTE | RENAL FAILURE ACUTE | RENAL FAILURE AND IMPAIRMENT | RENAL DISORDERS (EXC NEPHROPATHIES) | RENAL AND URINARY DISORDERS |
| CONCOMITANT DRUGS | NAME | DOSE | ROUTE | SUSPECT STATUS | |
| | ACURETIC | TAB QD | | YES | |
| | ATORVASTATIN | | | NO | |
| | ATACAND | 16MG QD PO ORAL | | YES | |
| | CEFIXIME | | | NO | |
| | NITRO-DUR | | | NO | |
| | TERBESMIN EXPECTORANTE | | | NO | |
| OUTCOMES: | HOSPITALIZATION-INITIAL OR PROLONGED (HO) LIFE-THREATENING (LT) | | | | |
| MANUFACTURER CONTROL CODE: | 19990200143 | | | | |
| MANUFACTURER DATE: | 1999-03-5 | | | | |
| ADVERSE EVENT DATE: | 1998-12-13 | | | | |
| REPORT TYPE: | EXP | | | | |
| REPORT SOURCE: | OTH | | | | |
| CASE SOURCE: | AERS | | | | |
| NARRATIVE: | | | | | |

| [CASE ID] | [SEX] | [MANUFACTURER CONTROL CODE] | [DA REPORT RECEIPT DATE] | [AGE] | DRUGS | REACTIONS | [SERIOUS] |
|---|---|---|---|---|---|---|---|
| 1 3510123 | F | 200010174BBE | 2000-06-1 | | TYLENOL, ALBUTEROL, DURATUSS G PM, ASPIRIN, ASULFAMETHOXZO EX BID, ASTELIN, LOTENSIN, ZYRTEC, DCELEBRAX, BENADRYL, PREMARIN, LASIX, HCL 2.5 MG, HYDROCODONE, IMMUNE GLOBULIN INTRAVENOUS (HUMAN), GAMIMUNE N 10%, PLACEBO, IODINE, XYLOCAINE, CLARITIN, GLUCOPHAGE, METHYLPREDNISOLONE, NASONEX, SINGULAR, PRILOSEC, OXYGEN, PAXIL, SOLUMADROL PACK, REZULIN 200 MG AM | CARDIAC MURMUR NOS; DYSPAPSIA; DYSPNORA NOS; OEDEMA LOWER LIMB; PAIN IN LIMB; PHLEBITIS NOS; PHYSICAL EXAMINATION NOS ABNORMAL; RHINORRHEA; TENDERNESS NOS; VENOUS THROMBOSIS DEEP LIMB | Y |
| 2 C01979033 | F | 97USA10861 | 1997-09-6 | | LOTENSIN | HYPERTENSION NOS; TABLET IN STOOL | N |
| 3 3204365 | F | 9806 1673 | 1998-08-26 | | ASPIRIN COATED; LOTENSIN, NIASPAN | ASTHENIA; DIZZINESS (EXC VERTIGO); DYSPEPSIA; FLUSHING; PAIN NOS | Y |
| 4 C01455473 | F | 9335 4001 | 1994-05-26 | | LOTENSIN | NAUSEA; VASODILATION | N |

METHOD AND SYSTEM FOR WEB-BASED ANALYSIS OF DRUG ADVERSE EFFECTS

BACKGROUND OF INVENTION

1. Field of the Invention

The present invention relates to a system and method for a web-based assessment and analysis of the risks of adverse effects resulting from the use of a particular drug, either alone or in combination with other drugs, nutrients, supplements, and other substances.

2. Description of the Related Art

In September 1997, information regarding cardiopulmonary disease related to the use of fenfluramine and phentermine ("fen-phen") prompted the United States Food and Drug Administration (FDA) to request the manufacturers of these drugs to voluntarily withdraw both treatments for obesity from the market. Subsequent studies show a 25 percent incidence of heart valve disease apparently resulting from diet drug use. Thus, up to 1,250,000 people may have sustained heart valve damage from these diet drugs and the FDA indicates that this may be the largest adverse drug effect the agency has ever dealt with.

Current estimates are that some 2.2 million hospital patients had serious adverse drug reactions and more than 100,000 people die each year from adverse reactions to prescription drugs. Accordingly, federal officials have recommended that the FDA require hospitals to report all serious drug reactions to the agency. The Inspector General of the Department of Health and Human Services has also indicated that the FDA should also work to identify harmful effects of new drugs and encourage health-care providers to rapidly call the FDA with information about drug side effects. As new drugs are introduced at increasing rates, the FDA will likely need additional resources to protect the public from hazardous drug side effects.

If one or two adverse drug reactions slip through the FDA's reporting process, the results can be tragic for some patients. That is especially true when the adverse reactions are rare but serious—such as in the case of liver failure caused by medication. All drugs have the potential to harm or kill the people they are designed to help. An injection of penicillin can kill in minutes if the recipient is allergic to this life-saving drug. Even common aspirin can be deadly.

Clinical trials of a new drug often involve a few hundred patients and therefore may not reveal that a drug can cause serious injury or death in one patient in 10,000 or even 1,000 patients. Accordingly, it is critical for researchers and drug companies to be able to analyze and predict adverse reactions among patients in their studies.

In addition, in clinical trials for drugs used to treat diseases such as diabetes, which affects so many people and is difficult to treat, FDA officials often face tremendous pressure to accelerate their approval process. Often, in this "fast-track" process, cases of adverse drug effects may slip through reporting procedures.

An even bigger challenge to the FDA is the occurrence of adverse drug reactions after the drug is on the market. In this case the drug is prescribed to a much larger population of patients, many of whom are taking other substances such as extracts, nutrients, vitamins, hormones or drugs that might have an adverse effect with the prescribed drug.

Thus, there is a need for effective analysis of adverse drug effects. Unfortunately, such a system has not been available.

U.S. Pat. No. 5,860,917 to Comanor et al., "Method And Apparatus For Predicting Therapeutic Outcomes" discloses methods, software, and systems for evaluating the response of a patient afflicted with a disease to a therapeutic regimen for the disease. In one aspect, the methods, systems, and software are provided for evaluating the utility of a treatment regimen for treating a patient afflicted with a disease. In one embodiment of this aspect, the value of at least one diagnostic variable relating to a statistical model describing the utility of the treatment regimen is determined. The statistical model is derived using a more robust similarity metric least squares (SMILES) analysis of the response to the treatment regimen which has been adapted to include discriminant and logistical analysis. The value of the diagnostic variable is then applied to the model to provide an estimated utility of the treatment regimen in treating the patient. Using the methods, software, and apparatus described therein, robust, statistically significant models of patient responsiveness that reduce the problems associated with present treatment response prediction methods that are brittle and oversimplify the complex interactions among treatment variables can assist patients and clinicians in determining therapies.

U.S. Pat. No. 6,000,828 to Leet, "Method Of Improving Drug Treatment" discloses a computer implemented method and system for improving drug treatment of patients in local communities by providing drug treatment protocols for particular disease states, such as Diagnosis Related Group (DRG) classifications. The protocol contains ranked recommendations for drug treatments of the disease state, and the computer system collects information about the risks and benefits of the drug treatments. The information collected about the treatments is used to modify the rankings of the drug treatments in the protocol. In one specific embodiment of the system, where the disease state has a microbial etiology and the treatments are anti-microbial drugs, the emergence of drug resistance is quickly detected by determining the percentage of microbial isolates that are found to be resistant to anti-microbial therapy in the community where the therapy is being provided (such as a community hospital or city-wide health care system). An increase in the percentage of resistant isolates produces a re-ranking of recommended drug therapies to avoid further use of the drug to which resistance has developed, and helps quickly introduce more effective drugs that will improve the effectiveness and lower the cost of treatment. In yet other embodiments, a sum of medication (e.g. dosing) errors and adverse effects (e.g. allergic reactions) are tracked by the system to identify drugs that are poorly tolerated in particular populations served by the hospital where the treatment is being provided. Data is collected about the safety and effectiveness of all types of drug therapies in the community being served, and this data is used to modify the drug protocols.

U.S. Pat. No. 6,014,631 to Teagarden et al., "Computer Implemented Patient Medication Review System And Process For The Managed Care, Health Care And/Or Pharmacy Industry" discloses an interactive computer assisted method for review and analysis of a patient who needs one or more medications. The method includes the steps of pre-selecting patients to obtain a preliminary set of patients eligible for the interactive computer assisted method responsive to first predetermined criteria, and filtering the preliminary set of patients to identify and form a secondary set of patients from the preliminary set of patients having a greater likelihood of benefiting from the interactive computer assisted method responsive to second predetermined criteria. The method includes the steps of enrolling a patient from the secondary set of patients, and communicating with the patient to obtain information to assist the user in determining whether therapy and/or medication issues are relevant. The method also includes the steps of preliminarily evaluating whether the therapy and medication issues are relevant responsive to the information, and communicating to a physician same. The method also includes the steps of determining whether the therapy and/or medication issues are relevant, and suggesting therapy changes, medication changes, or no changes for the patient.

U.S. Pat. No. 6,082,776 to Feinberg, "Storing Personal Medical Information" discloses a system and method for data compression of structured medical history information using multiple, updatable, static dictionaries in conjunction with an advanced probability-based model. The system is not a free text, word or phrase compressor as is presented in generalized or universal data compression systems. It employs a series of static dictionaries consisting of structured data developed from standardized medical classifications of disease, disorders, surgical procedures and medications. Prior probability information is utilized to achieve a high level of data compression of multiple data items at a time. The dictionaries are designed for flexible updating, efficient storage and retrieval, and data integrity. A portable medical card may be imprinted with the compressed medical information.

U.S. Pat. No. 5,737,539 to Edelson et al., "Prescription Creation System" discloses an electronic prescription creation system for use by professional prescribers at the point of care which has a prescription division subsystem permitting creation of a single prescription to be automatically divided into two components for fulfillment of one portion quickly and locally at higher cost and of another portion by remote mail order taking more time but providing a cost saving for a major part of the prescription. The prescription creation system has an ability to access remote source databases for system presentation to the prescriber of relevant, authorized and current drug, drug formulary and patient history information, with dynamic creation of a transient virtual patient record, the information being presented to the prescriber before completion of the prescription, permitting enhancement of the quality of prescribing decisions.

U.S. Pat. No. 5,845,255 to Mayaud, "Prescription Management System" discloses a wirelessly deployable, electronic prescription creation system for physician use which captures into a prescription a patient condition-objective of the prescribed treatment and provides for patient record assembly from source elements, with privacy controls for patient and doctor, adverse indication review and online access to comprehensive drug information including scientific literature.

Extensions to novel multi-drug packages and dispensing devices, and an "intelligent network" remote data retrieval architecture as well as onscreen physician-to-pharmacy and physician-to-physician e-mail are also provided.

U.S. Pat. No. 5,924,074 to Evans, "Electronic Medical Records System" discloses a medical records system that creates and maintains all patient data electronically. The system captures patient data, such as patient complaints, lab orders, medications, diagnoses, and procedures, at its source at the time of entry using a graphical user interface having touch screens. Using pen-based portable computers with wireless connections to a computer network, authorized healthcare providers can access, analyze, update and electronically annotate patient data even while other providers are using the same patient record. The system likewise permits instant, sophisticated analysis of patient data to identify relationships among the data considered. Moreover, the system includes the capability to access reference databases for consultation regarding allergies, medication interactions and practice guidelines. The system also includes the capability to incorporate legacy data, such as paper files and mainframe data, for a patient.

U.S. Pat. No. 6,219,674 to Classen, "System for creating and managing proprietary product data" discloses systems and methods for creating and using product data to enhance the safety of a medical or non-medical product. The systems receive vast amounts of data regarding adverse events associated with a particular product and analyze the data in light of already known adverse events associated with the product. The system develops at least one proprietary database of newly discovered adverse event information and new uses for the product and may catalog adverse event information for a large number of population subgroups. The system may also be programmed to incorporate the information into intellectual property and contract documents. Manufacturers can include the information in consumer product information that they provide to consumers or, in the case of certain medical products, prescribers of the medical products.

However, none of these references provides a web-based system and method for analyzing the risks of adverse effects resulting from the use of a particular drug, either alone or in combination with other substances, including but not limited to hormones, drugs, nutrients, and supplements.

Thus, there remains a need for a more efficient and effective system and method for web-based analysis of the risks of adverse effects resulting from the use of a particular drug, either alone or in combination with other substances including but not limited to hormones, drugs, nutrients, chemicals, toxins, foodstuffs, beverages, and supplements. There also remains a need for a more efficient and effective system and method for web-based analysis of the risks of adverse effects resulting from the use of a particular drug on particular segments of the population.

SUMMARY OF INVENTION

The system of the present invention is a web-based system for assessing and analyzing the risks of adverse effects resulting from the use of at least one drug of interest, comprising: a selector for identifying at least one drug of interest; a profiler for selecting from multiple profiles related to the safety of the at least one drug of interest, using at least one filter; at least one data mining engine; and an output device for displaying the analytic results from the data mining engine.

The present invention pertains to a computer-implemented method for assessing and analyzing the risks of adverse effects resulting from the use of at least one drug of interest, comprising: storing data regarding the risks of adverse effects from the use of at least one drug of interest in one or more servers linked to the Internet; updating such data regarding the risks with additional information pertinent to the risks of adverse effects from the use of the at least one drug of interest; permitting at least one remote user to access such data through the World Wide Web upon proper authentication; permitting the at least one remote user to identify the at least one drug of interest; permitting the at least one remote user to select data stored in the one or more servers relevant to the safety of using the at least one drug of interest; permitting the at least one remote user to analyze safety issues resulting from use of the at least one drug of interest; and permitting the at least one remote user to display such data and analysis.

The present invention also pertains to a computer-implemented method for assessing and analyzing the risks of adverse effects resulting from the use of at least one substance of interest, comprising: storing data regarding the risks of adverse effects from the use of at least one substance of interest in one or more servers linked to the Internet; updating such data regarding the risks with additional information pertinent to the risks of adverse effects from the use of the at least one Substance of interest; permitting at least one remote user to access such data through the World Wide Web upon proper authentication; permitting the at least one remote user to identify the at least one substance of interest; permitting the at least one remote user to select data stored in the one or more servers relevant to the safety of using the at least one substance of interest; permitting the at least one remote user to analyze safety issues resulting from use of the at least one substance of interest; and permitting the at least one remote user to display such data and analysis.

Preferably, the system and method of the present invention for web-based assessment and analysis of the risks of adverse effects resulting from the use of a drug of interest, either alone or in combination with other drugs, nutrients, supplements, and other substances comprises at least one data mining engine preferably selected from the group consisting of (1) a proportional analysis engine to assess deviations in a set of the reactions to the drug of interest, (2) a comparator to measure the reactions to the drug of interest against a user-defined backdrop, and (3) a correlator to look for correlated signal characteristics in drug/reaction/demographic information; and an output device whereby a user can receive analytic results from the selector, and the at least one data mining engine.

It will appreciated that such a system and method for assessing and analyzing the risks of adverse effects resulting from the use of one or more particular drugs is advantageous to the various risk assessors who are tasked with making such determinations. Such risk assessors include governmental agents who perform such assessment for regulatory purposes, agents of pharmaceutical manufacturers who are tasked with such assessments, health care personnel, such as physicians, nurses, anesthesiologists, as well as patients or anyone prescribed drugs or simply wondering about the safety profile of a particular drug, alone or in combination with other substances.

The Internet is a global network connecting millions of computers. As of 1999, the Internet had more than 200 million users worldwide, and that number is growing rapidly. More than 100 countries are linked into exchanges of data, news and opinions. Unlike online services, which are centrally controlled, the Internet is decentralized by design. Each Internet computer, called a host, is independent. Its operators can choose which Internet services to use and which local services to make available to the global Internet community. There are a variety of ways to access the Internet. Most frequently one gains access to Internet services through a commercial Internet Service Provider (ISP).

The World Wide Web (Web) is a system of Internet servers that support specially formatted documents. The documents are formatted in a language called HTML (HyperText Markup Language) that supports links to other documents, as well as graphics, audio, and video files. This means a user can jump from one document to another simply by clicking on hot spots. There are several applications called Web browsers that make it easy to access the World Wide Web; Two of the most popular being Netscape Navigator and Microsoft's Internet Explorer.

The Web permits web-based applications. Such web-based applications use TCP/IP and HTTP protocols to transport information from a central network application server to Web clients and back. The interface for the system could be the familiar unmodified Web browser, a Web browser customized with special features, or a unique Web application. These web-enabled applications can be designed to be a single, though massive, application. Navigational features, visual design, and information organization will be uniformly applied. In other web-enabled applications, the components may be designed independently and only linked by a central menued application.

The present invention, which provides a system and method for web-based assessment and analysis of the risks of adverse effects resulting from the use of one or more particular drugs, offers an enhanced degree of analysis not previously available. This enhanced degree of analysis permits the identification of associations and, thus, potential causal elements regarding adverse effects resulting from the use of one or more particular drugs.

The present invention provides answers to several key questions that are essential to public health. For example, various safety groups, both government and private, are charged with monitoring the post-market behavior of drugs and determining "signals" that indicate a relationship among adverse reactions, demographics, and other elements such as outcomes. Unexpected or previously unrecognized adverse drug effects can take the forms of single reactions, groups of reactions, or increases in a labeled reaction. A labeled reaction is a reaction to a drug previously reported to the FDA of such a degree that the FDA-proscribed label for the drug identifies such a reaction to the particular drug. Such adverse drug effects might be due to the higher exposure to the general population experienced in post-market therapy or such effects can be a reaction that has a demographic (genetic or otherwise) emphasis in an age or gender group.

Further, with efficient and effective analysis of adverse drug effects, pharmaceutical research and development professionals can learn more details of the reaction profiles of drugs and the at-risk populations who may be prescribed those drugs. This information would allow a more effective selection of lead compounds and would produce drugs with less risk of adverse effects.

Additionally, the web-based analysis of adverse drug effects of the present invention permits multiple users to concurrently assess the hypotheses regarding the possible existence and causation of the adverse drug effects.

The web-based analysis of adverse drug effects of the present invention also permits users to assess hypotheses regarding the possible existence and causation of the adverse drug effects on a continuous, real-time basis, 24 hours a day, 7 days a week.

The web-based analysis of adverse drug effects of the present invention further permits users to access the application world-wide, without any geographic limitation.

Additionally, the web-based analysis of adverse drug effects of the present invention further permits the application to be run from a server and accessed by standard browsers, thus obviating the need for special software or downloads.

The above-described geographic and coherent/consistent advantages permit greater cooperation among researchers, even if affiliated with different organizations.

Further, the web-based analysis of adverse drug effects of the present invention permits the databases which provide the data regarding adverse drug effects to be updated at regular intervals and to be available for all users at the same time. In addition, such databases (and the application, as well) is maintained in one consistent, coherent format so that all users are employing the same version.

In addition, the web-based analysis of adverse drug effects of the present invention permits alerting of users of emerging issues and standards. Thus, the present invention permits faster response to public health emergencies.

Thus, the present invention provides analysis of adverse drug effects with enhanced speed and flexibility. The present invention also offers new insights with regard to adverse drug effects and augments the existing processes of drug development.

Accordingly, it is an object of the present invention to provide a more efficient and effective system and method for web-based analysis of the risks of adverse effects resulting from the use of a drug, either alone or in combination with other drugs, nutrients, supplements, chemicals, toxins, foodstuffs, beverages and other substances.

It is an object of the present invention to provide a more efficient and effective system and method for web-based analysis of the risks of adverse effects resulting from the use of a drug.

It is further an object of the present invention to provide a more efficient and effective system and method for web-based analysis of the risks of adverse effects resulting from the use of a drug in combination with another substance.

Yet another object of the present invention is to provide a more efficient and effective system and method for web-based analysis of the risks of adverse effects resulting from the use of a drug in combination with another substance, wherein the substance is a nutrient, vitamin, hormone, chemical, toxin, foodstuff, beverage or drug.

An advantage of the present invention is that potential adverse effects to the health of a human or animal may be predicted and avoided.

Yet another object of the present invention is to provide a more efficient and effective system and method useful for web-based analysis of the risks of adverse effects resulting from the use of a drug, alone or in combination with another substance, wherein the substance is a nutrient, vitamin, hormone, or drug, further wherein the system and method can be used by providers of medical or veterinary care services.

Another object of the present invention is to provide a more efficient and effective system and method useful for web-based analysis of the risks of adverse effects resulting from the use of a drug, alone or in combination with another substance, wherein the substance is a nutrient, vitamin, hormone, chemical, toxin, foodstuff, beverage, or drug, further wherein the system and method can be used by consumers of medical care services.

A greater understanding of the present invention and its concomitant advantages will be obtained by referring to the following figure and detailed description provided below.

BRIEF DESCRIPTION OF DRAWINGS

FIG. 5 is a representation of a selector page of the present invention;

FIG. 6 is an illustration of an exemplary pedigree screen of the present invention;

FIG. 8 is a representation of a concomitant drugs table in the profiler component of the present invention;

FIG. 9 is a depiction of a demographics table in the profiler component of the present invention;

FIG. 10 is an illustration of a report dates table in the profiler component of the present invention;

FIG. 11 is a representation of an outcomes table in the profiler component of the present invention;

FIG. 12 is a depiction of a reaction filter screen of the present invention;

FIG. 13 is an illustration of a correlation results screen of the present invention;

FIG. 14 is a representation of a correlation details screen of the present invention;

FIG. 15 is a depiction of a case details screen of the present invention;

FIG. 21 is a representation of a case list of the present invention.

DETAILED DESCRIPTION

The present invention provides a system and method for web-based assessment and analysis of the risks of adverse effects resulting from the use of one or more particular drugs, either alone or in combination with other drugs, nutrients, supplements, vitamins, foods, beverages, and other substances.

The primary components of a preferred embodiment of the present system and method for analysis of adverse drug effects are a combination of the following: one or more integrated databases; a selector for selecting at least one drug for analysis (based on the generic, brand names or therapeutic category); a profiler for displaying statistics that describe behavior for the drug in multiple dimensions; at least one filter and the means to control the at least one filter individually and in combination with other filters; at least one of multiple data mining engines preferably selected from the group of a correlator, a proportional analysis engine, and a comparator; and a graphical user interface for displaying the results of the analysis.

For purposes of the present invention, a substance shall be understood to include one or more elements of the set of drugs, foodstuffs, beverages, nutrients, vitamins, toxins, chemicals, hormones, and supplements.

Figure 1:
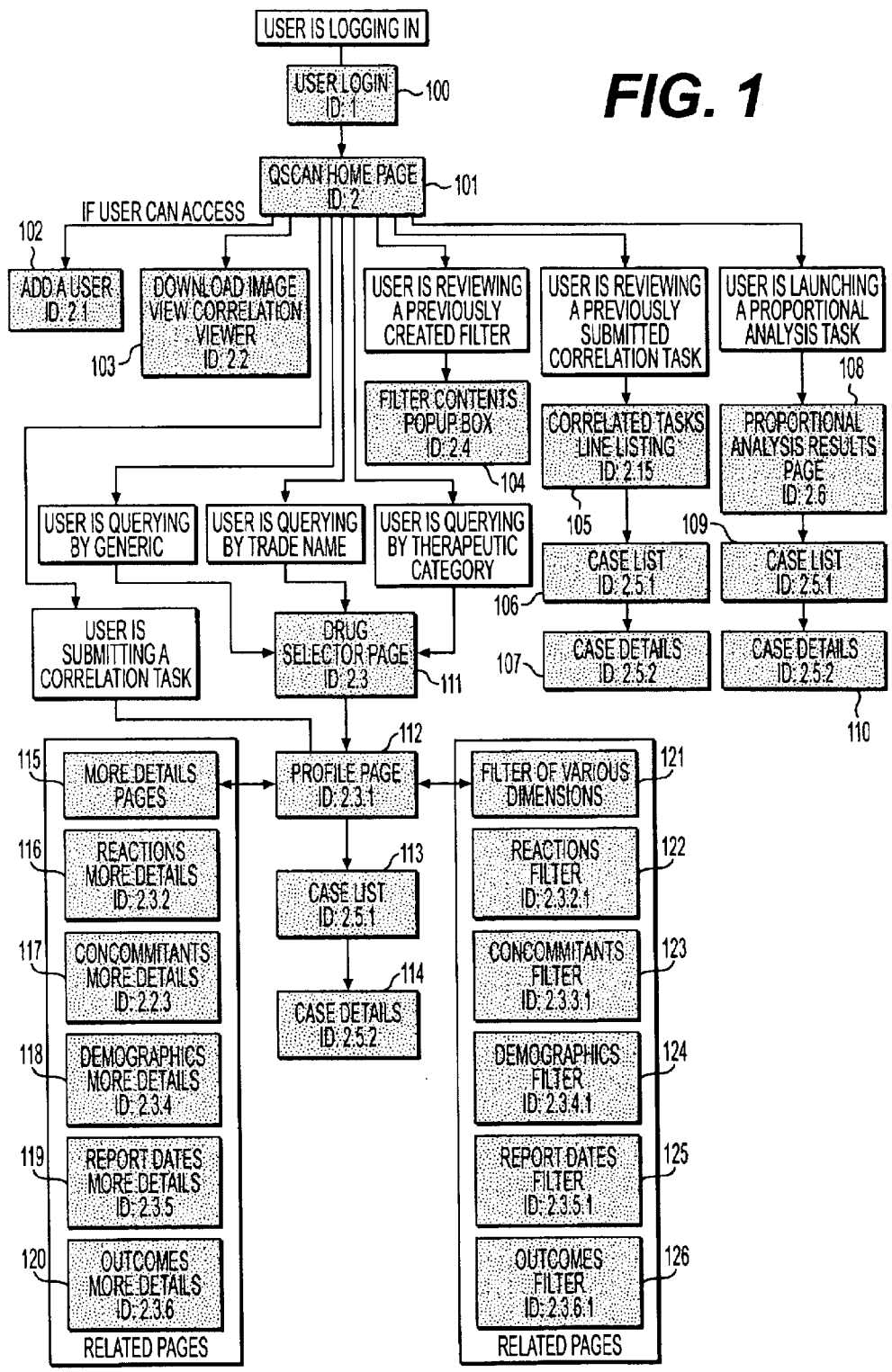
FIG. 1 is chart indicating the page flow of the present invention.

A preferred page flow of the present invention is indicated in FIG. 1. Box 100 represents a user login window. If the user successfully logs in and is authenticated, then the user is then placed in the home page 101 of the present invention. From the home page 101, the user can add a user at the Add a User Box 102; download an data image at the ImageView Correlation Viewer Box 103; review a previously created filter at the Filter Contents Pop-up Box 104; review a previously submitted correlation task at the Correlated Terms Line Listing Box 105;

launch a proportional analysis task at the Proportional Analysis Results Page Box 108; or query the system with regard to a drug at Drug Selector Page Box 111. It will be appreciated that the user can query regarding a drug by generic name, trade name, or therapeutic category.

Preferably, if the user is reviewing a previously submitted correlation task at the Correlated Terms Line Listing Box 105, then the present invention permits the user to access the case list at the Case List Box 106 and, further, permits the user to drill down on individual elements in the case list and obtain case details at the Case Details Box 107.

Preferably, if the user is launching a proportional analysis task at the Proportional Analysis Results Page Box 108, then the present invention permits the user to access the case list at the Case List Box 109 and, further, permits the user to drill down on individual elements in the case list and obtain case details at the Case Details Box 110.

Preferably, if the user is querying the system with regard to a drug at Drug Selector Page Box 111, then the present invention permits the user to access the drug profile at the Profile Page Box 112, further, permits the user to access the case list at the Case List Box 113 and, still further, permits the user to drill down on individual elements in the case list and obtain case details at the Case Details Box 114.

From the Profile page Box 112, the user preferably can either access more details regarding the various dimensions of the risk assessment at the More Details Box 115 or filter in various dimensions of the risk assessment at the Filter in Various Dimensions Box 121.

If the user has chosen to access more details, then the user is preferably presented with multiple dimensions of the risk assessment from which to access more information. Preferred dimensions of risk assessment include, but are not limited to, Reactions More Details Box 115, Concomitant Drugs More Details Box 116, Demographics More Details Box 118, Report Dates More Details Box 118, and Outcomes More Details Box 120.

Preferably, if the user has chosen to filter in various dimensions of risk assessment, then the user is preferably presented with multiple filters for the dimensions of the risk assessment. Preferred filters of dimensions of risk assessment include, but are not limited to, Reactions Filters Box 121, Concomitant Drugs Filters Box 122, Demographics Filters Box 123, Report Dates Filters Box 125, and Outcomes Filters Box 126.

Figure 2:
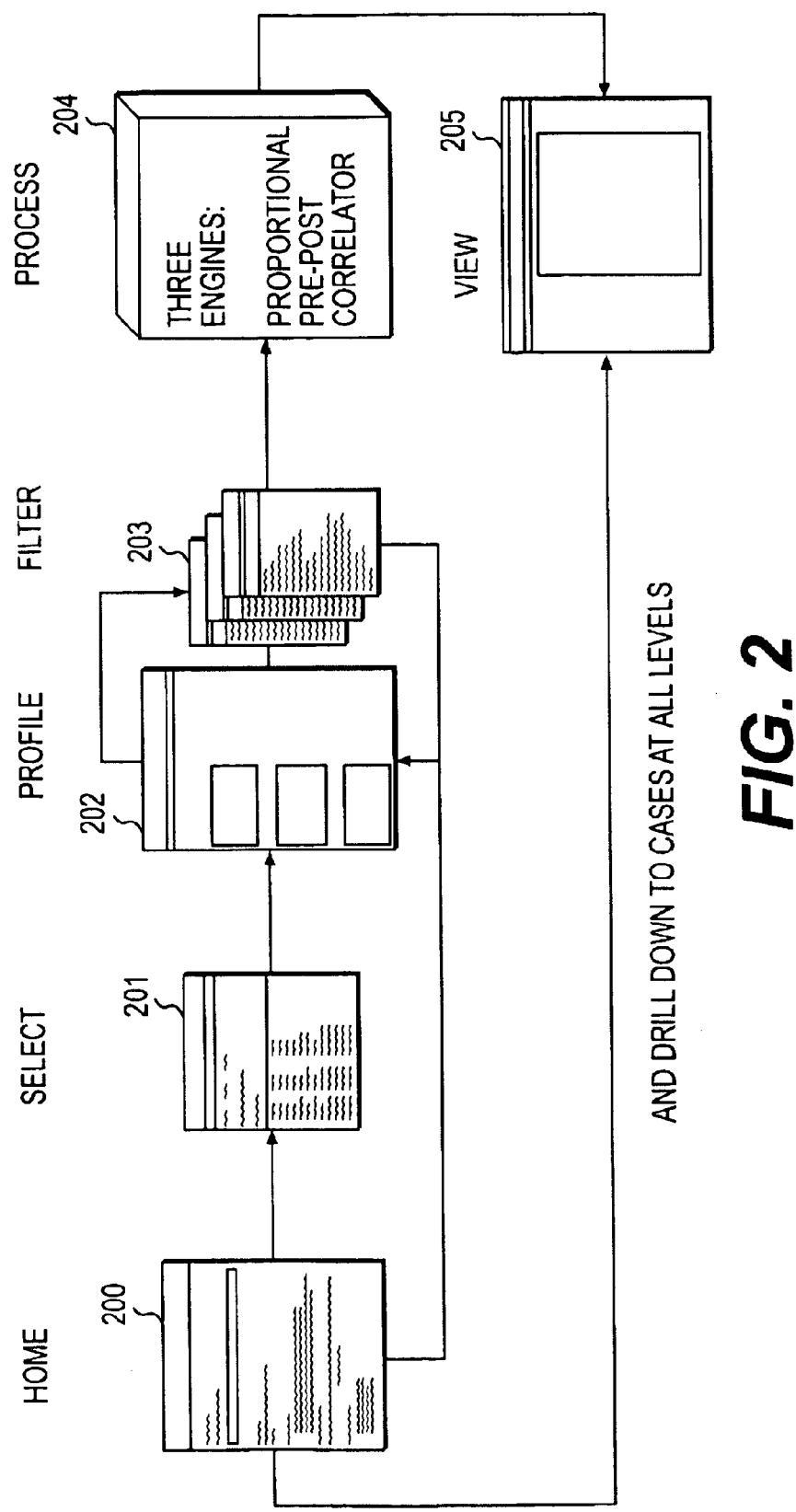
FIG. 2 is an overview of the present invention.

The preferred components of the present invention are illustrated in FIG. 2, which provides an overview of the system and method of the present invention. The user preferably accesses the system of the present invention by means of Home Page 200. From Home Page 200 the user can proceed to the Selector 201, where the user can select a drug for analysis. Having selected the drug of interest, the user can then preferably proceed to the Profiler 202, which preferably displays statistics that describe the behavior of the drug of interest. From the Profiler 202 the user can then preferably proceed to employ one or more Filters 203, which permit recalculation of the statistics by selecting among the available variables. Once a set of cases is determined, for example, by the use of one or more filters, the cases can then preferably be submitted to at least of three or more Data Mining Engines 204. The output from the data mining engines is then preferably displayed in a Viewer 205, which can present the data in a variety of formats, including, but not limited to a sortable table, a sortable line listing, and a radar screen, thus, allowing rapid identification of signals and providing the user the ability to drill down to individual case details.

Alternatively, in another preferred embodiment, from Home Page 200 the user can choose a profile from the Profiler 202, apply one or more Filters 203, process the set of cases using the Data Mining Engines 204 and display the results with the Viewer 205.

Computer systems typically include operating system software that control the basic function of the computer, and one or more software applications that run under the control of the operating system to perform desired tasks. As the capabilities of computer systems have increased, the software applications designed for high performance computer systems have become extremely powerful.

Other changes in technology have also profoundly affected how computers are used. For example, the widespread proliferation of computers prompted the development of computer networks that allow computers to communicate with each other. With the introduction of the personal computer (PC), computing became accessible to large numbers of people. Networks for personal computers were developed to allow individual users to communicate with each other. In this manner, a large number of people within a company could communicate simultaneously over a network with a software application running on a single computer system.

One significant computer network that has recently become very popular is the Internet. The Internet grew out of the modern proliferation of computers and networks, and has evolved into a sophisticated worldwide network of computer systems linked together by web pages that collectively make up the "world-wide web", or WWW. A user at an individual PC (i.e., workstation) that wishes to access the WWW typically does so using a software application known as a web browser. A web browser makes a connection via the WWW to other computers known as web servers, and receives information from the web servers that is displayed on the user's workstation. Information displayed to the user is typically organized into pages that are constructed using one or more specialized languages, for example, Hypertext Markup Language (HTML).

The present invention is implemented conveniently in an Internet or Web-based computer network. Thus, in a representative Web client/Web server a client machine is connected to a Web server platform via a communication channel.

For illustrative purposes, the communication channel is the public Internet, an intranet, an extranet or any other known network connection. Web server platform is one of a plurality of servers which are accessible by clients. A representative client machine may include a Web browser, which is a known software tool used to access the servers of the network. The Web server platform supports files in the form of hypertext documents, graphics and other data type objects. The network path to a server (or to a file on the server) is identified by a Uniform Resource Locator (URL), as is well-known.

A representative Web Server platform comprises a computer running the NT Operating System and a Web server program, such as Netscape Enterprise Server Version 3.51, that supports interface extensions. The platform also includes a graphical user interface (GUI) for management and administration, and an Application Programming Interface (API) to enable application developers to extend and/or customize the core functionality thereof through software programs known as "plug-ins." The system and method of the present invention is similar to an application offered by an Application Software Provider (ASP). ASPs are entities that manage and distribute software-based services and solutions to users across a wide area network from a central data center.

A representative Web client is a personal computer, includes an operating system such as Microsoft Windows, as well as a browser, such as Netscape Communicator (any version) or Internet Explorer (any version), having native support for application plug-ins. The Web client machine is connectable to the Web server(s) via the Internet, an intranet or some other computer network. The Web client browser typically includes a Java Virtual Machine (JVM), which provides a convenient runtime environment for programs written as Java applications or applets.

Although not required, the present invention is preferably implemented as a Java application or applet (i.e. a set of Java program instructions or code) that is downloaded to or otherwise delivered to a machine (on a tangible medium) and installed in a known manner.

Although the Web client is typically a personal computer, this is not a requirement. The Web client may be any generalized "information appliance" having a processor, an operating system, optionally a browser application, and a means to connect the device to a computer network from which data may be retrieved. Such appliances include, without limitation, a handheld or palmtop device (e.g., running Windows CE 2.0 or higher), a diskless or so-called "network computer", a set-top computer terminal, or the like.

Generalizing, the assessment method of the present invention may be implemented in any remote distributed node connectable to a center operating at a server node. A query at the remote distributed node is assessed according to the invention using an "iterative session" between the remote distributed node and the server node. An iterative session refers to set of communications back and forth between the node and the center by which a solution to a technical problem is reached. A session may involve only one "pass" or iteration although, more typically, several iterations will be required to move toward an assessment at the client node.

Although numerous system architectures may be used to implement the inventive technique, one particularly advantageous architecture is implemented, for example, in a corporate enterprise environment (such as an intranet), wherein a plurality of client machines (desktops) interface with a support center located at a server node through a network. The clients are the desktop machines used by the community of application end users. Typically, client machines are separated from the network via a firewall. Each client machine may include conventional browser software.

Preferably, the present invention operates on at least one of two integrated databases: an external public database characterized by breadth of data across all drugs and a database containing internal data of an organization or an individual characterized by increased detail with regard to one or more specific groups of drugs. It will be appreciated that a database containing the internal data of an individual can refer to a number of different situations, including but not limited to the biological/medical/genetic/demographic/environmental/behavioral/drug sensitivity of an individual.

In both cases, the source and purpose of the data may vary, including post-marketing surveillance, clinical trial data, health care system data, research databases, and literature, among others.

The public database preferably is at least one database selected from either a combination of one or more of the FDA's Spontaneous Reporting System (SRS)(after to November 1997)) and the FDA's Adverse Event Reporting System (AERS)(after to November 1997)), the World Health Organization adverse event database, or other country-specific regulatory or epidemiological databases, such as the UK Advert system and the General Practice Research Database (GPRD). These public databases are updated regularly as they release new case data. In a related invention, which is a particularly preferred embodiment of the present invention, the present system and method for analyzing adverse drug effects relies upon a derivative of these public databases that has cleaned, parsed in to a relational database, and mapped to known dictionaries, and standardized for efficient searching and query defining. This preferred derivative database has over 2 million cases representing 30 years of adverse events as reported to regulatory authorities. Additionally, the derivative database links the adverse event (AE) case data to Medical Dictionary for Regulatory Activities (MedDRA), Coding Symbols for a Thesaurus of Adverse Reaction Terms (COSTART), and World Health Organization (WHO) Adverse Drug Reaction Terminology (WHOART), among others for reactions, and the National Drug Code Directory (NCDC), Orange Book or WHO Drug dictionaries for drugs. The invention includes the facility to substitute and manage standard dictionaries for all dimensions.

In a preferred embodiment, the present system and method also operate on a database containing internal data of an organization. For example, such an internal database could be the proprietary database of a pharmaceutical company or the contemporaneous database of a clinical investigator during the course of clinical trials upon a drug.

It will be appreciated that one preferred embodiment of the present invention utilizes a log-on screen. Access to the present invention is provided by means of the Web. The present system and method preferably supports all browsers including Netscape and Internet Explorer for access. In a particularly preferred embodiment, different URLs are used for the public database and for the internal database. This allows operating in two databases concurrently if two instances of the Web browser are opened. It also allows virtually unlimited simultaneous processes, and simultaneous processing at various locations.

The use of multiple sessions also enable a range of comparisons, in each and every dimension. The "differencing engine" or comparator provides immediate information on similarities and differences.

The web-based aspect of the assessment of adverse effects of one or more drugs of the present invention permits the user to discern patterns of causation.

The web-based aspect of the assessment of adverse effects of one or more drugs of the present invention also permits two or more users to collaborate in the assessment. A useful feature of such collaboration is the ability to have an expert assist another user in the assessment of adverse effects of one or more drugs. For example, one user, perhaps more experienced in the use of filters, could select one or more filters to apply to the data, while another user, more familiar with diagnosis related groups, reviews the billboards of results. Thus, the web-based analysis permits users with different skills to collaborate.

A related collaboration involves the ability of the present invention to provide both the web-based product and the web-based services. A user, upon completion of his/her analysis, can communicate the results of his/her analysis in a variety of formats, including report format, and screen format, among others. Such communication can be carried out by means of the Web.

It will be appreciated that such a web-based assessment of adverse effects of one or more drugs of the present invention permits an advantageous revenue model, in which the user pays a subscription fee for use of the web-enabled method of the present invention.

The web-based aspect of the assessment of adverse effects of one or more drugs of the present invention also permits multiple simultaneous users. This feature of the present invention is important in assessors who, although working for the same organization, are in different locations.

Another aspect of the web-based aspect of the assessment of adverse effects of one or more drugs of the present invention is that it permits syndication of the databases regarding the data of adverse effects of one or more drugs.

A further aspect of the web-based aspect of the assessment of adverse effects of one or more drugs of the present invention is that it permits a user to send data from one analysis to another user for review.

Further, the web-based analysis of adverse drug effects of the present invention permits the databases which provide the data regarding adverse drug effects to be updated at regular intervals and to be available for all users at the same time.

In addition, the web-based analysis of adverse drug effects of the present invention permits alerting of users of emerging issues and standards.

The web-based analysis of adverse drug effects of the present invention also permits enhanced security. The use of one or more levels of encryption permits the present invention to offer a high level of security.

Another important aspect of the web-based analysis of adverse drug effects of the present invention is the ability to associate hyperlinks with each piece of data. For example, within the application, it is possible to link each number, name, entry, and selectable point with additional information.

Yet another advantage of the web-based system and method of the present invention is the ability of a user to run simultaneous sessions on the same data, thus increasing efficiency and permitting the testing of parallel but different hypotheses in real-time.

The present invention also provides an enhanced ability to test several hypotheses simultaneously.

The present invention further provides the ability for a group of users to construct a collaborative workgroup.

In another preferred embodiment of the present invention, a home screen is used to launch searches, and review results of the analytical engines and prior work. For example, from the home screen a user can (1) select a drug to study by either name or by therapeutic category, (2) recall a previously saved filter (that was created, named and saved previously, (3) review previously submitted analyses, or (4) invoke certain data mining engines directly. An exemplary version of a home page of the present invention is provided in FIG. 3. From this home screen, the user can use field 301 to select a drug to study by generic name, trade name, or therapeutic category. The user can also use field 302 to recall a previously saved query (called a filter). Further, the user can use field 303 to recall previously submitted analyses. Additionally, the user can use field 304 to invoke the proportional analysis engine.

The home page is preferably the user's command center for analysis. The home page is preferably always accessible from any other screen.

Preferably, the home screen has four areas. The first area is a link to the selector, thus, allowing a user to easily reach the drug selection screen through any level of detail on a drug. The second is a filter area. The user can view and apply previously saved filters. The third section is the data mining engine section which allows a user to invoke one or more of the data mining engines. The fourth area permits the user to review previously generated analyses.

With regard to the selection of a drug, this feature allows a user to select at least one drug to study and to search for information on that at least one drug by using either its generic name, its trade name, its therapeutic category, or its chemical name. In addition, the invention provides the ability to develop specific other valuable taxonomies, such as a "super generic" including all salts of a drug, or a sub-brand, for example distinguishing between a once a day version of a drug from a once a week version of the drug.

Concerning selecting a previously saved query, this feature (referred to as a filter) is a preferred paradigm to reduce the routine of inputting a previously employed and saved query. By establishing parameters for searching, a user does not need to define ad hoc queries. Knowledge of pharmacovigilance is used to present users with filter/query-building interfaces that are more in line with the thought processes and paradigms employed by such users. A user can preserve the set of parameters of a query (a filter) each time he/she refines a profile, and further, a user can employ a filter he/she has developed in a previous search the next time he/she wishes to view the same or an updated set of cases.

Figure 4:
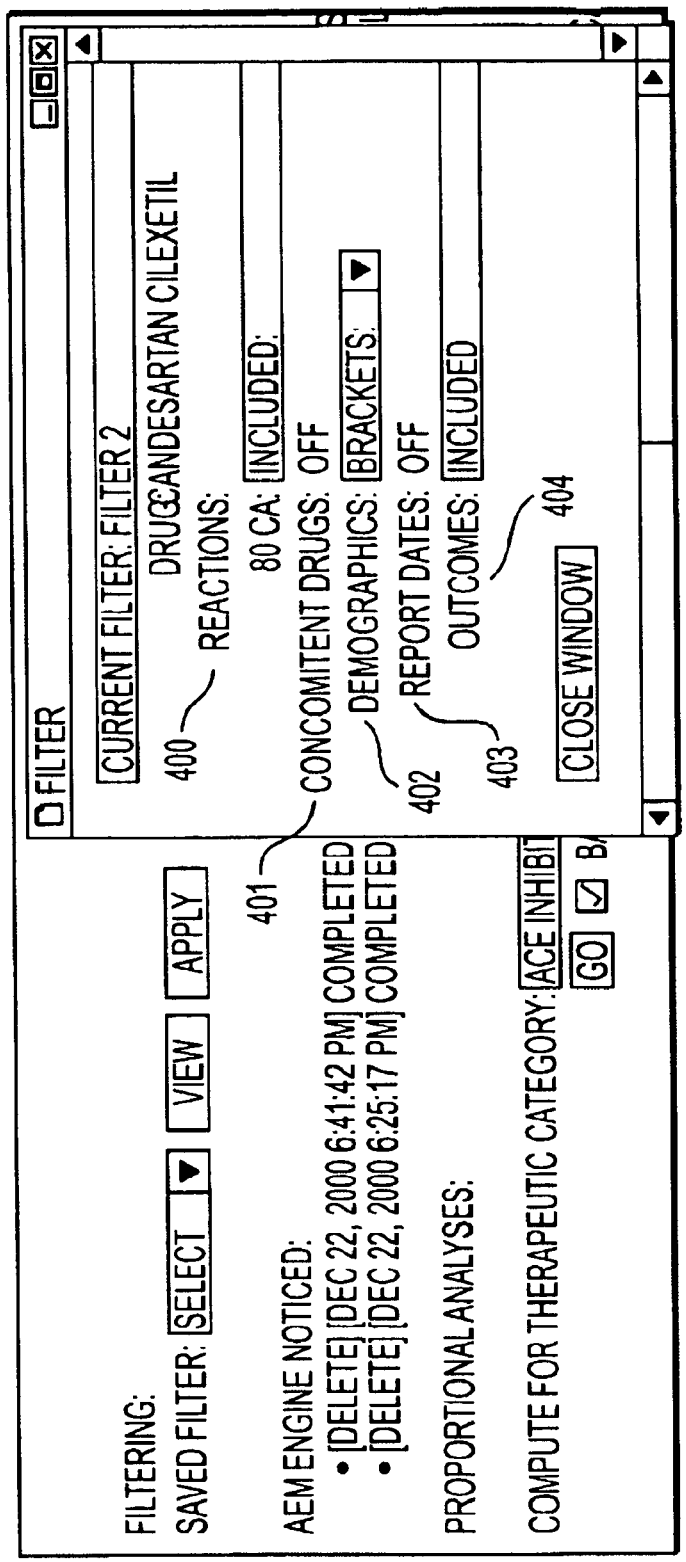
FIG. 4 is a representation of a filter selection page of the present invention.

For example, FIG. 4 provides a representation of a preferred filter screen. Various preferred fields of a filter screen are presented, including, but not limited to, Reactions (field 400), Concomitant Drugs (field 401), Demographics (field 402), Report Dates (field 403), and Outcomes (field 404).

In invoking a saved filter, a user is offered the option of viewing or applying (querying with) a saved filter, and a pull-down menu allows a user to select one of the filters previously created and saved. Pushing the "View" button allows a review of the specific details of the filter. In the example provided, a user had created and saved a filter he/she had labeled "Filter 2" for a search on Candesartan Cilexetil. The search results show the drug's Reactions, including its MedDRA Hierarchy Group (System-Organ-Class (SOCs), etc.), and a pull-down menu showing the specific reactions (ear and labyrinth disorders, for example) included in the filter.

Case sets, as well as drug sets, can be created, named, and saved similar to filters. Because these case sets generate a list rather than a logic description, viewing and changing are performed with a list manager. Filters, drug sets, and case sets can all be combined or merged to provide a rich set of functions, and great flexibility.

The preferred parameters of a filter include reactions (listed as "included" or "off"); concomitant drugs (listed or "off"); demographics (listed as per previously set brackets or "off"); report dates (listed or "off"); and outcomes (listed or "off"). If a user wishes to apply this saved filter as his/her current query, he/she would click on the "Apply" button. At this point, a user would be taken to the profile screens for that drug and that set of filters.

Figure 3:
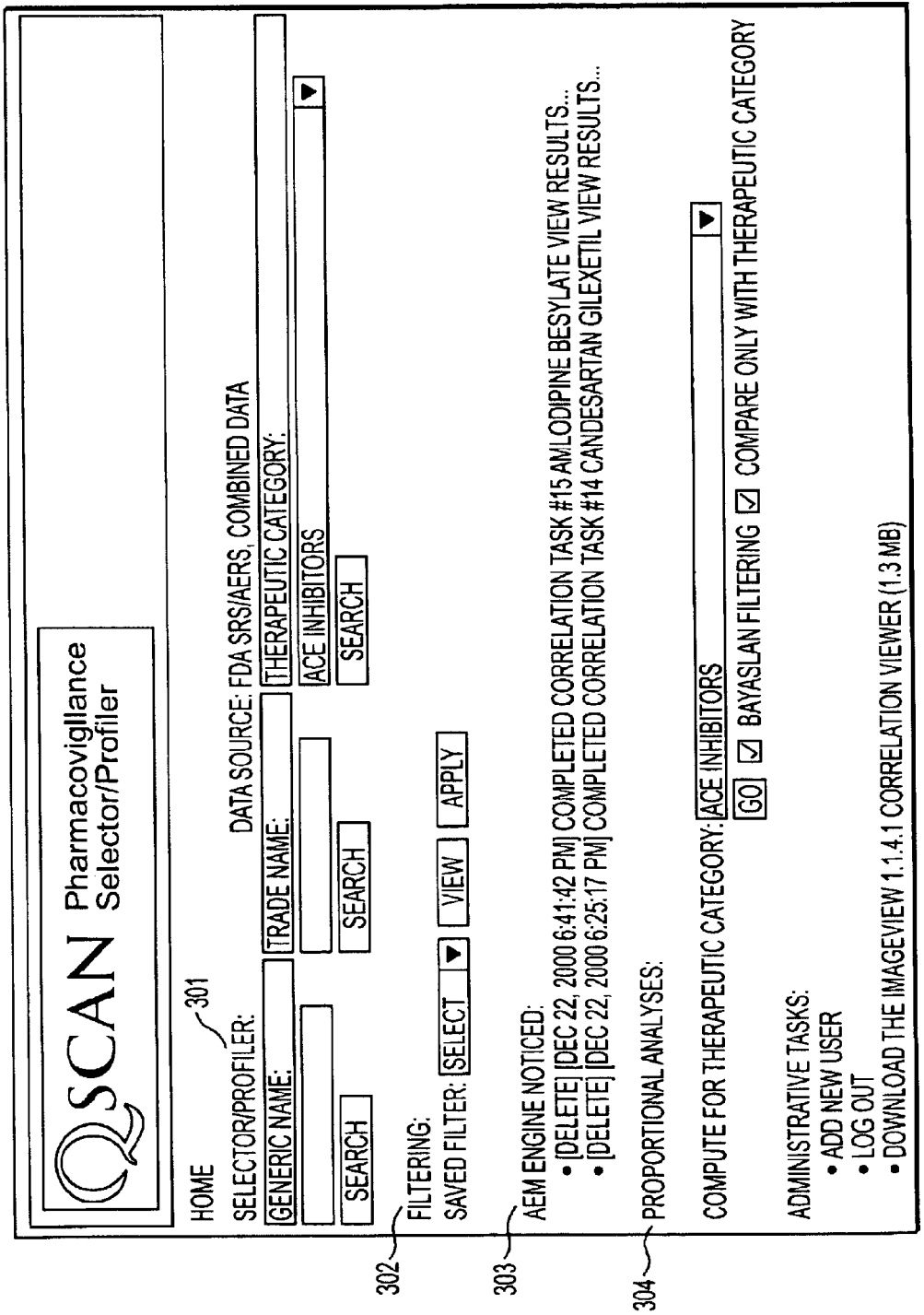
FIG. 3 is a depiction of a home page of the present invention.

With regard to the review of the previous analysis aspect of the present invention, this section of the home page provides information on previous analyses a user has run using the correlator engine of the present invention. As illustrated in FIG. 3, the correlator engine notices provide information on analyses that have been previously completed including date and time, task number, and generic drug. Each listing ends with a hyperlink that a user can employ to view the results of the search. A "delete" function is preferably provided to manage this list.

Concerning the proportional analyzer aspect of the present invention, this component looks for large or small deviations in the reactions counts for a set of drugs, i.e., comparing drugs to those in their own therapeutic category or to all drugs. With a preferred embodiment of the present invention, a user has an option to compute for a therapeutic category using a pull-down menu. A user also has an option of selecting Bayesian filtering. Bayesian filtering employs a statistical cut-off threshold to reduce the effect of rows or columns with a very low number of cases. That is, drugs or reactions accounting for less than a certain percent of cases or fewer than a set number will be deleted from the matrix (and so noted on the results screen).

A user preferably has two options in running this analysis: (1) he/she can compute information for each drug's reactions in comparison with all of the drugs in the system; or (2) a user can run an analysis by comparing the selected drug's reactions only with those of other drugs in the same therapeutic category. Results are preferably presented concurrently on a separate screen.

An additional preferred aspect of this home page is a comparator, which is available when a user is accessing optionally provided clinical trial data from a drug label, or from the clinical trial data of an internal database. The comparator compares potential and actual adverse effects of drugs in the pre- and post-market environments.

The preferred home page of the present invention also provides a user with the options to add a user, manage preferences, manage the group of inserts, and to log out, among others.

If a user has selected a query at the Home page, he/she will initiate a query for a drug using the drug's generic name, its trade name, its therapeutic category, its chemical name, or other custom-defined categories. The search invokes the selector page of the present invention. A user selects a drug by clicking on the generic drug link which then takes a user to the profile and general statistics regarding the selected drug. A user starts his/her search on the home screen, and then continues it on the selector page, by entering or selecting the category of drug he/she wants to search: the generic name, the trade name, the therapeutic category or the custom-defined categories. The therapeutic category field preferably has a pull-down menu to help identify and select the desired field.

An exemplary Query Screen page is illustrated in FIG. 5, where a user has decided to search the therapeutic category of angiotensin converting enzyme (ACE) inhibitors, as defined by the drug dictionaries. (Note: In this case the FDA taxonomy places certain drugs known as ATII drugs in the ACE category.) Here, the user has chosen not to use the generic name field 500 or the trade name field 501, but rather has chosen the therapeutic category field 503. The present system returns with the hits corresponding to the selected therapeutic category and are displayed in the query screen. In this example, 22 drugs matching the search criteria were found in the "ACE Inhibitors" category. The drugs are listed in alphabetical order by their generic name. For each generic drug on the list, all trade names and all relevant therapeutic categories are presented in pull-down menus. Optionally, custom-defined categories can also be shown. The search results also allow access to the drug's "pedigree," or lexical mapping information, indicated by a question mark link.

Preferably, a user can stop browsing drugs and go directly to the profile by selecting and applying a previously stored filter.

With regard to the pedigree function, if a user selects the pedigree icon for the selected drug (the question mark in this example), a user is presented with the drug's pedigree, which shows the way the drug has been mapped in a drug dictionary and thesaurus.

An exemplary pedigree screen is presented in FIG. 6. This exemplary pedigree screen provides a number of preferred fields indicating the cataloging of the data in the system of the present invention. Preferred fields include, but are not limited to, Map To (field 600), Verbatim (field 601), Source (field 602), Incidents (field 603), Case Count (field 604), QEDRX Processing (field 605), Cross-Reference (field 606), and First/Last Reported Reactions (field 607). The data pedigree search not only shows how the drug is catalogued in the present invention, it also shows the drug's mapping to known dictionaries. These data are displayed in a tabular form, and indicate the logical route from verbatim terms to the "map to" terms used to search the database. This function informs the user of specific ranges, types of corruption and number of each type of corruption in the data that have been corrected.

For example, a preferred pedigree screen of the present invention provides categories including Map to, Verbatim, Cross-Reference, Incidents, Case Counts, QEDRX Processing, First/Last Reported Reactions, and Source. The Map to category shows how the verbatim name was mapped to a generic or trade name. The Verbatim category shows the verbatim name the drug was found under in the database. This can be any form of the name under which this drug was found in the FDA database, and includes misspellings, variations, etc. The Cross-reference category indicates which data source contains this verbatim, the SRS database or the AERS database, etc. The Incidents category indicates the number of times this verbatim appears in the database. The QEDRX Processing category refers to the "cleanup" performed on the data. The specific processing steps are defined in a key. The Source category indicates which reference data source was used to map this verbatim to a generic.

The key explains the types of processing that the system and method of the present invention performs to standardize drug names and to improve the quality of the reported data. The present invention preferably performs five types of processing: spelling correction (corrects misspelled drug names and standardizes variations in drug names), noise words (words like, for example, "tablets" "Prozac tablets" does not offer further information about the drug itself; it simply provides information on how the drug was administered), combo words (alphanumerics like "20 mg.," for example, which are redundant because already in the database), numerics (the "20" in 20 mg. In this case, 20 is a numeric and "mg" is a noise word), marks (extraneous typographic symbols, such as brackets, dashes, and so forth). Additional aspects of this feature of the present invention are provided in U.S. patent application Ser. No. 09/681,587 filed May 2, 2001, entitled Pharmacovigilance Database, which is incorporated herein by reference.

The profiler aspect of the present invention permits a user to navigate various dimensions of the selected drug's safety profile and view cases, concomitant drugs, reactions, demographics, outcomes, and time intervals using specified filters. Once a user is satisfied with the cases profiled, the set of cases satisfying the filter criteria can then be submitted to the various data mining engines, including the Correlator Engine (CE), Proportioning Engine (PE) and Differencing Engine (DE). Each data mining engine is provided with a set-up and a verification step (by means of a page set of input parameters). For example, the CE may further weight the different dimensions.

It will also be appreciated that the profiler of this invention allows for continuous adjustment and addition to the dimensions. For example, a preferred embodiment includes "Repeat Source". Others may contain laboratory results. The invention permits expanding and contracting both the profiler and the at least two filters as the data changes.

As noted above, in the selector component of the present invention, each of the drugs in the generic name category is preferably presented in a format that indicates a hyperlink. Clicking on a generic drug (in the previous example Candesartan Cilexetil), the multi-dimension profile screen is invoked by clicking on a generic drug (in the previous example Candesartan Cilexetil).

The idea of profiling a drug is complex, because of the multiple dimensions. The invention's profiler separates presenting data on the selected drug into several different categories and preferably "billboards" the top ten for immediate visibility. It will be appreciated that the user can specify any number for "billboarding." At the top of the screen are the generic name of the drug (preferably with a hyperlink to its pedigree), all the trade names associated with the drug, and all of the therapeutic categories to which it belongs.

The profile feature of the present invention is used to display statistics that describe the effects of the drug in multiple dimensions. Each set of data is preferably presented in a separate table, headed by an index tab. The preferred data sets include, but are not limited to: (1) Reactions; (2) Concomitant Drugs; (3) Demographics; (4) Report Dates (for example, dates logged by FDA as report dates for SRS and AERS); and (5) Outcomes.

For each dimension there are key actions: all allow filtering and delving for more details. The filter action allows a user to set and activate filters for that dimension. The "More Details" action brings up all the values that have appeared only in the top 10 billboard style on the main page.

For certain dimensions, for example reactions, the hierarchy of the dimension can be selected to change the billboard and detailed views. In the case of reactions, MedDRA contains a five level hierarchy. Other dictionaries use two to four levels. The present invention accommodates the full range of hierarchies.

Preferably, the profiler feature of the present invention allows grouping concomitant drugs by therapeutic category, chemical class, or other custom-defined class.

With regard to the Reactions dimension, the profiler component of the present invention preferably shows reactions to the drug that is being queried. This dimension refers to suspected adverse reactions to the selected drug that were reported. A suitable reactions table is provided in FIG. 7. In this figure, to the right of the Reactions tab is a pull-down menu labeled "View" 700, followed by a filter hyperlink 701. By utilizing the pull down menu, a user can choose among multiple different levels of MedDRA. Of these multiple different levels of MedDRA, four are particularly preferred. These are System, Organ, Class (SOC), High Level Group Term (HGLT), High Level Term (HLT), and Preferred Term (PT).

Figure 7:
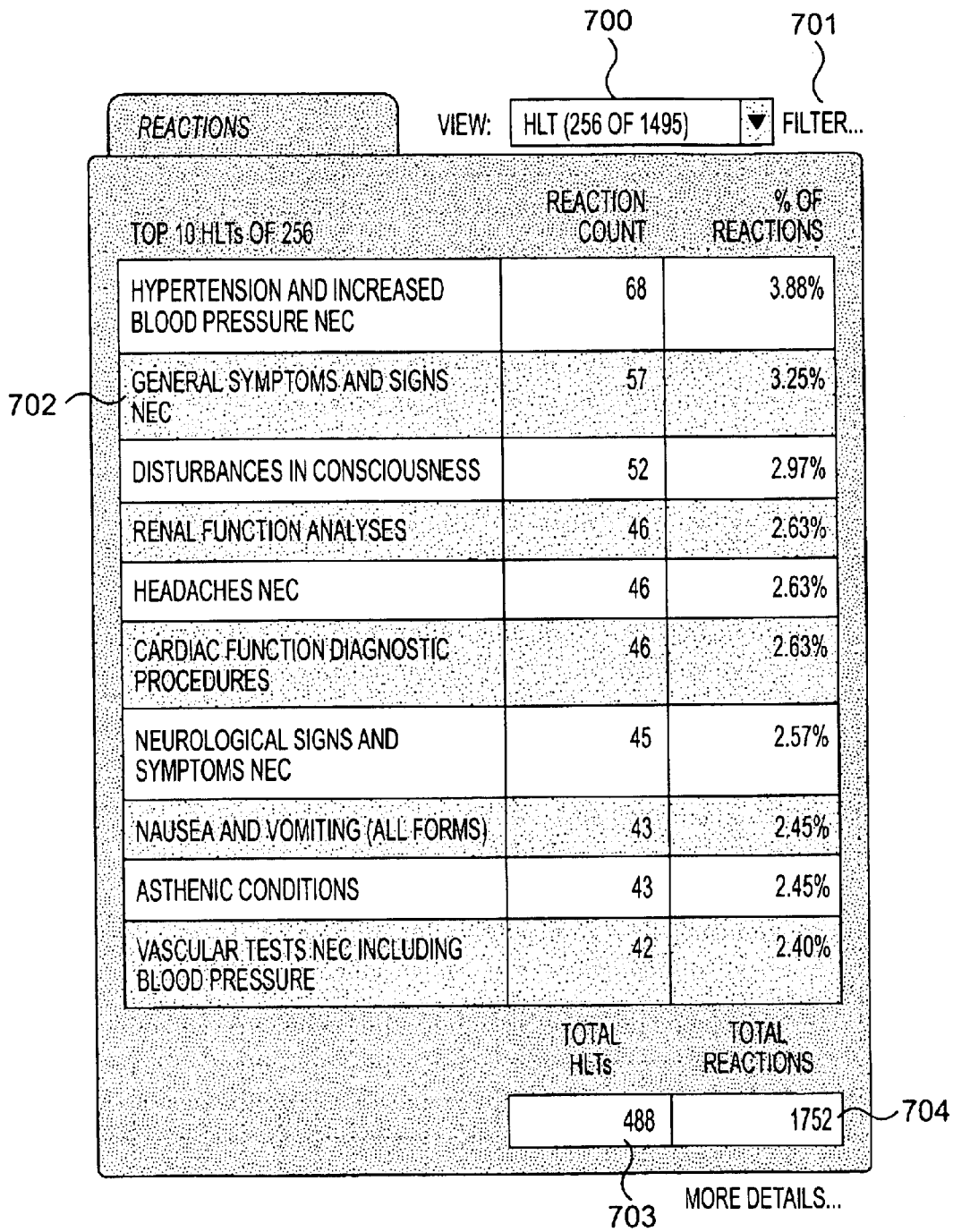
FIG. 7 is a depiction of an exemplary reactions table in the profiler component of the present invention.

In FIG. 7, a user has chosen the HLT option. The window in the pull-down menu indicates that there are 256 HLTs out of the total of 1495 HLTs in the current version of MedDRA. The Reactions Table 702 shows the Top 10 HLTs of the 256. In this case, the reactions include hypertension, disturbances in consciousness, and so forth. For each of the reactions, the table presents the Reaction Count (the number of times this reaction was listed in the database) and the percentage of reactions that this number constituted in the set of reactions for this drug, based on incidents of reactions (not cases).

At the bottom of the Reaction Count and % of Reactions columns are numbers showing the number of incidents of the reactions at the Top 10 HLTs (488) and the Total Reactions across all of the 256 HLTs (in this case, 1752), 703 and 704, respectively.

The ability to browse statistics, up and down a hierarchy, and within real time, is important to keeping risk assessment hypothesis setting and testing within a short period of time. The invention provides extensive associative tables and reverse indexing to enable such rapid analysis.

A hyperlink offering more details concurrently follows the Reactions table, and brings up a separate page with all details of this dimension.

It will be appreciated that since Reactions, Concomitant Drugs, and Outcomes are summarized at the event level, the resultant collection of cases will be different if more than one event is associated with a single case. For example, if two reactions are recorded in a single case, and both of those reactions parent to the same MedDRA SOC, then they will account for two events, and yet would yield only a single case in the case listing.

In a preferred embodiment of the present invention, case level percentages and percentage relative to drug exposure are also available in the profiler component of the present invention. With regard to the Concomitant Drugs dimension of the profiler of the present invention, this dimension describes drugs that were also prescribed in the cases in which the target drug was found. A suitable example of a Concomitant Drugs table is provided in FIG. 8.

In this figure, the Concomitant Drugs Table 800 lists the top 10 drugs in the concomitant category. In this example, hydrochlorothiazide, aspirin, and furosemide were among the drugs found in combination with Candesartan Cilexetil in the adverse reactions reported to the FDA.

The table divides the cases of concomitant drugs into two groups: Suspect and Non-suspect (fields 801 and 802 respectively). When an adverse reaction report is filed, certain drugs in the case may be indicated as suspect. When considering concomitant drugs, these drugs will be either suspect or not in the cases relating to the queried drug (in this case, Candesartan Cilexetil). Thus, in this example there are four cases to consider, suspect and non-suspect for the queried drug, and suspect and non-suspect for the concomitant drug.

In the example, Hydrochlorothiazide is the drug found to be most frequently interacting with Candesartan Cilexetil. The total number of incidents (45) is broken out into the Suspect and Non-suspect categories, and the total is also displayed as a percentage of cases that mention this concomitant drug (it is assumed a drug is only mentioned once per case), in this case 10.79% of the total number of cases involving Candesartan Cilexetil. The remaining Top 10 concomitant drugs are listed in order of descending frequency.

Because it is difficult to predict the number of drugs that are reported, the drug detail section provides browser paging and sorting. Paging and sorting are techniques of the invention used to "bubble to the top" the significantly hypothesized items.

Concerning the Demographics dimension of the profiler component, this table provides demographic information about the population included in the query. An appropriate demographic table in the profiler of the present invention is provided in FIG. 9. Preferably five age groups, ranging from below 16 to above 75, are included in field 900. The data is also preferably broken out by gender (field 901). The category totals and percentages are also provided. The detailed listing gives the statistics by single age rather than by generational grouping.

Regarding the Report Dates dimension of the profiler component, report dates for the incidents included in the selected drug query are presented. A suitable report dates table is presented in FIG. 10. In the example, the time interval (field 1000) is the decade 1990–1999 and shows the number of reports in each of those years for the drug Candesartan Cilexetil.

The time interval of the incidents included in this query is presented in this table. In the example, the time interval is 1990–1999 and shows the total number of reports for that period (field 1001)(446) and the percentage (field 1002)(in this case, 100.00%) of reports for the drug Candesartan Cilexetil that fall within that time interval. By selecting the more details link, a user can obtain the breakdown of the reports by individual years.

In the Outcomes dimension of the profiler of the present system and method, case outcomes are listed. An appropriate outcomes table is presented in FIG. 11. Preferred categories include serious outcomes such as congenital anomaly, death, and disability, as well as other outcomes. Serious outcomes are preferably presented in red, while less- or non-serious outcomes are in black. The Outcomes Table provides a table of outcomes (field 1100), a count (field 1101) and percentages of the outcomes (field 1102) in each category, as well as totals of serious and non-serious outcomes.

The filtering feature of the present invention is a paradigm that reduces the routine of constructing ad hoc queries. This filtering feature is context-sensitive and relieves a user of the burden of repeatedly defining the parameters of the queries. Filtering allows a user to formulate queries in a way more consistent with paradigms used by medical professionals, selecting among the active cases and using standard dictionaries such as MedDRA and National Drug Code Directory. This filtering features preferably allows a user to apply and view filters individually, set filters as a group and apply globally, or save and apply filters at a later time.

Data is compiled by the filters selected for each analysis. In the above example, filters were established for the reaction query. One of the screens in the profiler component was the reactions dimension, providing the Top 10 SOCs for the drug Candesartan Cilexetil. At the top of the table was a pull-down menu with "View" selected, also provided with a filter hyperlink.

Each of the data sets in the Profiler (Reactions, Concomitant Drugs, Demographics, Report Dates, and Outcomes) provides a user with the opportunity to establish filter parameters in any order. In a preferred implementation, the invention tabs the individual filters for convenience, and allows merging with other filters.

Figure 12:
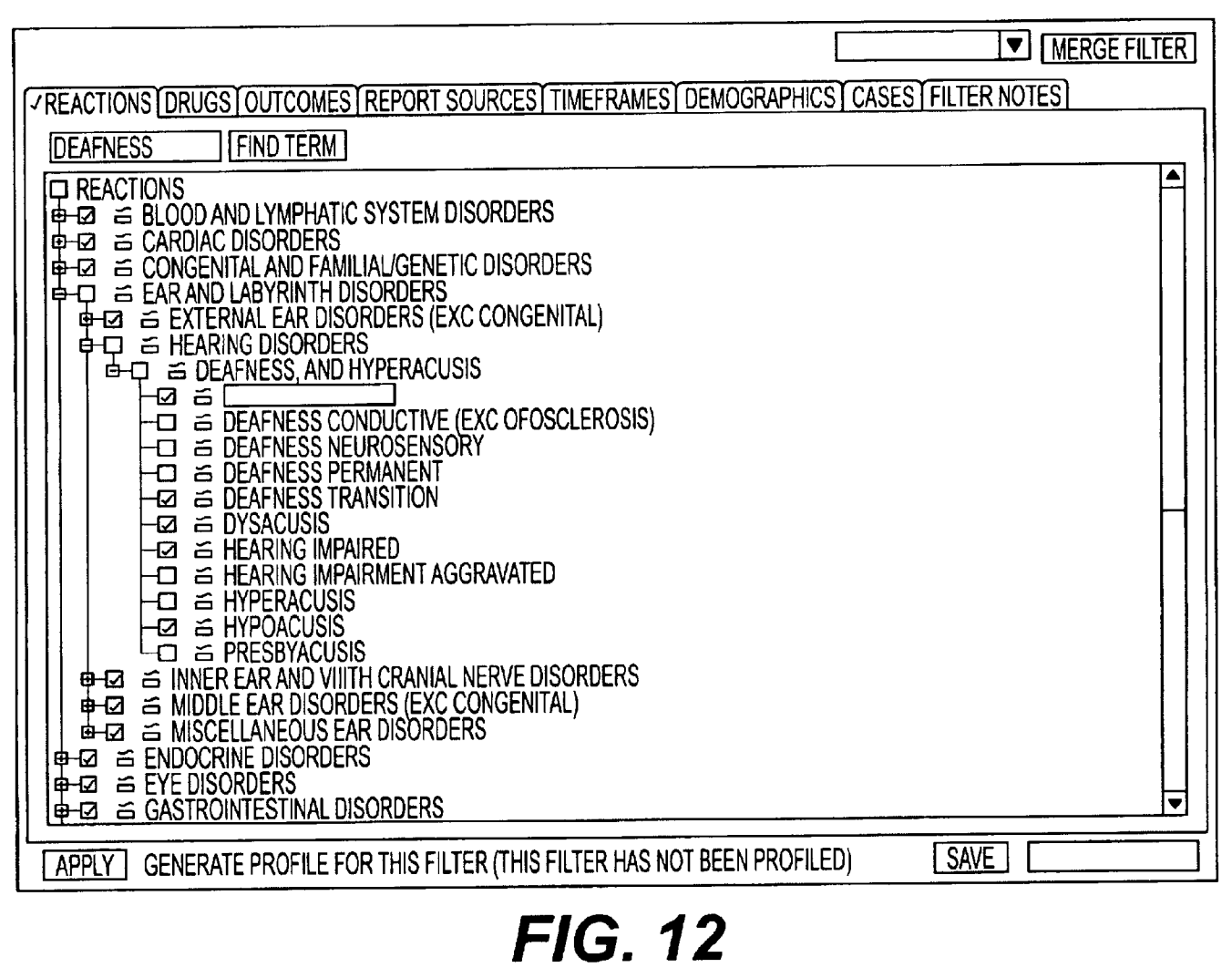

An exemplary filter applied as to reactions is provided in FIG. 12. This figure provides the list of Reaction Filters available for profiling. The filter is based on the MedDRA hierarchy and begins at the SOC level.

The mechanics for working with filters is common to all dimensions. A user may click on any or all of the reactions they would like to have included in the filtered reaction profile.

In the example of Reaction filtering, clicking on an SOC brings up the HLGTs for that SOC and allows selection at that level.

In a preferred embodiment filtering can be done at all levels.

It will be appreciated that for the more complex filters, such as the reaction filter, a range of user friendly aids is provided. For displayed MedDRA leads, preferably a tree is used. When it is collapsed, an open box preferably means no selections lower in the hierarchy have been identified, a check means all lower selections in the hierarchy have been identified, and a new query box is used to indicate unchecked box(es) somewhere below in the hierarchy.

Another preferred feature of the present invention is content-based pre-filters. To make it easier to switch-off indication-related adverse drug reactions, an "indications-related" button is preferably provided in the selection. For labeled adverse effects, of which there could be hundreds, the invention preferably provides tables (in this case with data from drug labels) to switch off all of the labeled reactions. This quickly focuses the user's attention on "unexpected" reactions.

Preferably on the profiler component, the present invention monitors the contents of each filter as it is built. At any point, the filter can be saved as an entirely new filter or by overwriting an old one, or changing and saving an incremental filter. This permits fine tuning of hypotheses regarding adverse drug reactions.

The filter for the concomitant drugs dimension allows selecting or deselecting any and each of the concomitant drugs reported in the profiled set of cases. Similar to reaction filtering, the concomitant drug dimension filter preferably provides a context selector (for example, to switch out a whole therapeutic category).

The demographics filter allows selections of generational or individual age brackets, and male/female selections as well. Generational filters are preferably user definable.

The report dates dimension allows selection by bracketed years. In addition, in another embodiment of the invention, the report dates filter incorporate a link to a drug's birth date and allow filtering by "first six months," "first two years," etc. A table of drug birth dates relieves the user of the need to separately enter those dates.

The Outcome filter allows individual outcome selection, or by serious/nonserious grouping. For internal database adverse events, if a custom seriousness set is defined, this dimension will be user definable.

The analysis provided by the system and method of the present invention finds "signals" such as anomalies in a random population, a change against a known background, or a coherent target in a noise background. This is accomplished by at least one of three or more data mining engines: the proportional analysis engine (PE), the comparator (differencing engine or DE), and the correlator. In a preferred embodiment, the proportional analysis engine can be invoked from the home screen, as can be the comparator, for selected data. The correlator is invoked after filtering cases from the profile page.

The correlator looks for the association of characteristics in literally millions of pieces of drug/reaction/demographic information concurrently.

Too often in risk assessment, important correlations are hidden by surrounding background "noise" that obscures connections among data elements. Using a multidimensional vector analysis, the correlator measures the degree of association among pairs of values (for example, a drug and a reaction, an age and an outcome, etc.). The correlation algorithm is user selectable and definable. The preferred version uses a Pearson product-moment correlation known conventionally as "$R^2$". Other algorithms can also be used. The invention preferably applies the correlation after filtering, greatly enhancing the signal and reducing noise.

As a preferred example, the profiler screen can provide a number of hyperlinks choices, including "Apply Filter" and "Compute Correlations." Selecting "Compute Correlations," a user initiates the correlator engine, using the active set of cases, based on the filter in use. While the processing is being carried out, a user is preferably returned to the home screen, where a message alerts a user that the correlation is being executed. Once the analysis is completed, a user is notified that the correlation has been completed and providing a user with the option to view the correlation results.

FIG. 13 provides an exemplary screen presenting the results of a correlated search. The line listing of correlated terms (which may be several screens in length) consists of the top 200 (this cut-off number can be any number that the user specifies and is selectable and sortable) sets of correlated terms for a user's analysis on the requested drug. The data compares the correlations between "Term 1" and "Term 2." For each pair of terms, the screen preferably shows its relative rank (field 1303); score (field 1304)(the term-pair's correlative value relative to other term-pairs, for example, "Female" and "Candesartan" are more "associated" than any other pair of terms, for example, in the set of cases containing "Female" and "Candesartan," were relatively highly correlated); the identity of the first term (field 1300) and the category to which it belongs (field 1305); and the identity of the second term (field 1301) and the category to which it belongs (field 1306).

Although the product moment correlation has been employed in a number of areas, it has typically been used for numerical data. The invention sends the correlator a vector comprised almost entirely of categorical terms, a new and previously unexplored use of the Pearson $R^2$. The present invention's structural database, its ability to keep a consistent vocabulary (to name categories of a categorical variable) and its ability to provide sufficiently cleaned data regarding adverse drug reactions make the correlation meaningful. The present invention's ability to sort results, compare significance and handle thousands of cases was not available in the prior art. Since the correlator calculates association strength for both known factors (for example, age and gender) and rare reactions (for example, adverse drug reactions (ADR's)), this invention can identify meaningful relationships not otherwise easily observed.

In addition to viewing the table listing online, a user may also preferably select to review the results using a "radar-screen" correlation viewer. On the correlation screen, after the "Below are the top 200 correlated terms for your analysis . . . ," there is preferably a hyperlink that provides the option of viewing the results with the correlation viewer. In addition to viewing with the correlation viewer, a user is also preferably presented with options to save the file.

Two other information screens preferably provide additional information provided by the correlation engine. From the correlated terms screen, a user is preferably presented with hyperlinks comprising all of the numbers in the Rank column. A significance (to a user-selectable "P" value) is also preferably provided. These hyperlinks provide a link to individual case lists. An exemplary correlation details screen is provided in FIG. 14.

The Correlation Details screen of FIG. 14 provides the data for each of the cases included in that pair of correlated terms. For example, if the term pair in the Correlated Terms Screen was "Female" and "Candesartan Cilexetil," this screen provides the pertinent information for all of the cases where those two terms were paired. In this example, there were 18 cases where renal function analyses were correlated with Candesartan Cilexetil. For each case, preferably the following information is provided: the case ID (field 1401); the gender of the patient (field 1402); the Manufacturer's Control Code (field 1403); the FDA Report Receipt Date (field 1404); the patient's age (field 1405); the other drugs the patient was taking at the time of the incident(s)(field 1406); the patient's reaction(s) to the medications (field 1407); and whether the outcome was Serious (yes or no) (field 1408). By selecting these cases, the user can then profile the set of cases.

Additionally, to learn the details of a specific case, a user preferably can click on the case ID number of any case on the Correlation Details screen. The resultant information is preferably presented in a case details screen. An suitable case details screen is presented in FIG. 15.

The Case Details screen of FIG. 15 provides detailed information on each specific case. In addition to standard information such as the patient's case ID (field 1501), gender (field 1502), and age (field 1503), it preferably includes Reactions (field 1504)(including detailed information in the As Reported, Preferred Term, High Level Term, and High Level Group Term categories); Concomitant Drugs (field 1505)(each listed by Name, Dose, Route, and Suspect Status); Outcomes (field 1506); Manufacturer Control Code (field 1507); Manufacturer Date (field 1508); Adverse Event Date (field 1509); Report Type (field 1510); Report Source (field 1511); Case Source (field 1512), and Narrative (field 1513), if any. All data, including lab test and genetic information can be encoded and displayed.

It will be appreciated that the above-identified information is not the only information that can be provided; extra information fields may be also provided.

Figure 16:
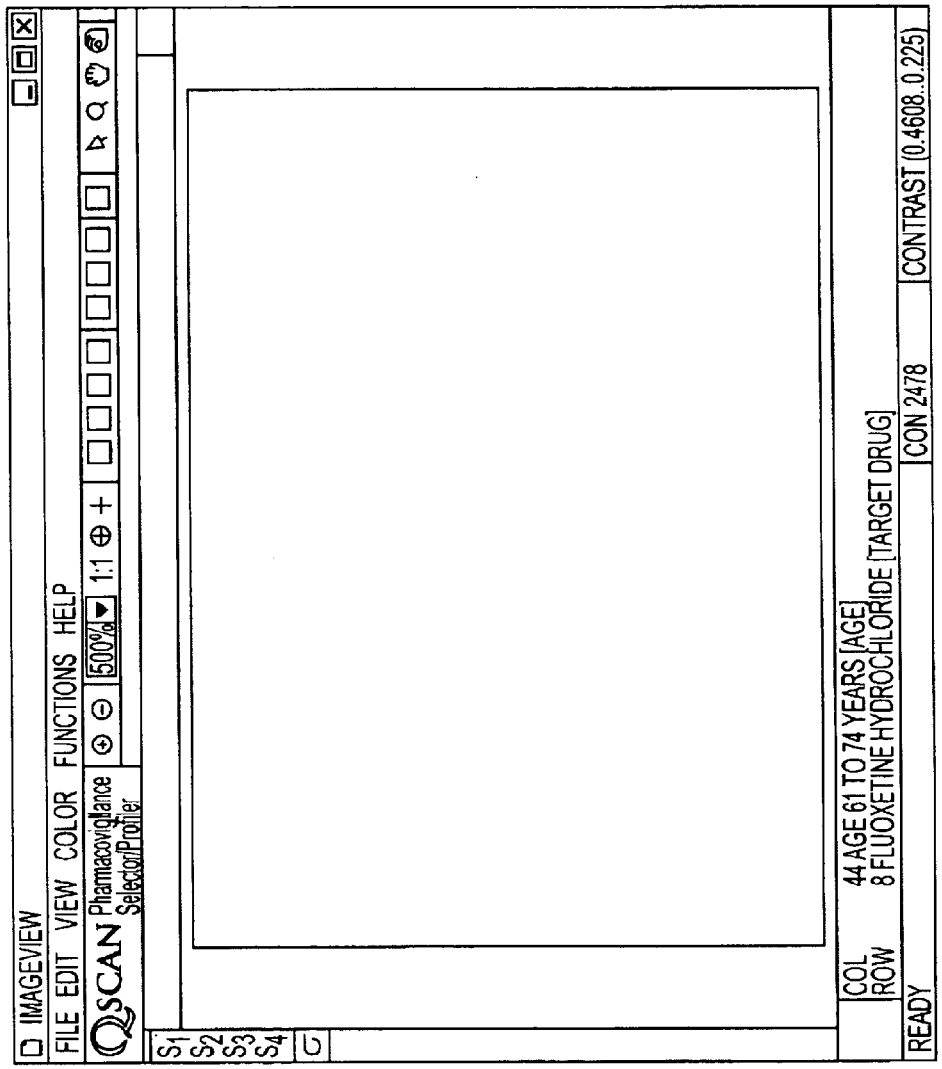
FIG. 16 is an exemplary illustration of a radar screen display of the present invention.

The adverse effect analysis result of the present invention are preferably presented in a format that provides both traditional tabular displays (line listings) and innovative "radar-like" displays. By populating a radar screen with textual information, a user moves from the cumbersome reading of printouts to the instant perception of correlations directly on the screen. Once a signal is identified, a case browser permit a user to move through user-defined sorting to the key cases involved. Once again the synergistic aspects of the invention come into play. A "Therapeutic Category" or "Labeled Reaction" selector can group the data on the radar screen to enhance the signal. An exemplary radar screen display is presented in FIG. 16.

The proportional analyzer engine of the present invention monitors outliers among reactions for drugs, for example, by comparing drugs to all drugs or those in a therapeutic class. The proportional analyzer engine can employ a variety of algorithms, including, but not limited to, PRR, ODDS ratio, and PRE, among others.

The proportional analyzer is preferably invoked from the home screen. A user is, in a preferred embodiment, prompted to select a therapeutic category for analysis by the proportional analyzer engine. Alternatively, a drug or a drug set can be selected. A user can select the therapeutic category that contains the drug he/she wishes to analyze. Bayesian filtering is preferably available as an option to remove noisy results due to lower case counts from the analysis.

In a preferred embodiment of the present invention, a user is prompted as to how he/she would like to analyze the drugs and reactions against the reaction counts of all drugs in the system, or only against their peers in their therapeutic category. The invention again allows cross-operation of its elements. So, for example, a set of cases can be filtered to use a background for the proportional analysis or a specific case set can be defined.

Figure 17:
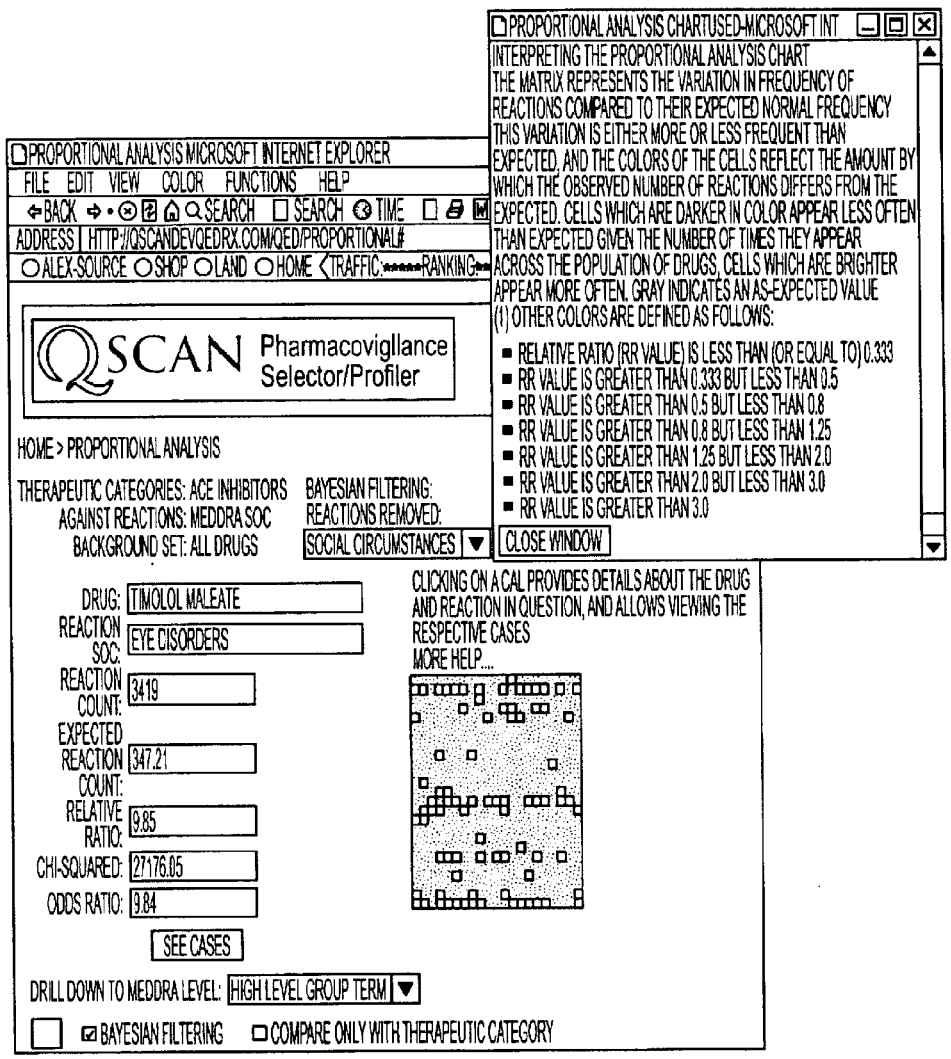
FIG. 17 is an illustration of a proportional analysis selection screen of the present invention.

Upon completion of the proportional analysis, a proportional analysis screen preferably presents the results. An exemplary proportional analysis screen is presented in FIG. 17. As presented in the figure, this screen preferably has several components, including, but not limited to a matrix showing the results for the relative ratios; a data block; and a line listing of the highest 100 relative ratios.

Preferably the proportional analysis screen presents the results of the analysis as a colored matrix of cells, indicating the frequency of reactions of various drugs compared to their expected normal frequency. The variation is either more or less frequent than expected, and the colors of the cells reflect the amount by which the observed number of reactions differs from the expected amount. Cells that are more darkly colored indicate reaction reporting lower than expected; cells that are gray indicate an as-expected value (or a Relative Ratio (RR) of 1); and cells that are more brightly colored indicate a greater Relative Ratio; the "hotter" the color (yellow to orange to red), the higher the frequency of reactions.

A user may preferably select any cell in the matrix for further information. Selecting a specific cell provides details about the drug (field 1800) and its reaction (field 1801), including also the reaction count (field 1802), the expected reaction count (field 1803), and the Relative Ratio between the two (field 1804). An example of the proportional analysis results screen is provided in FIG. 18.

The invention also allows "analytical drill down". That is, the ability to redo the analysis, in a preferred case, for a drug and a reaction system-organ-class. The user then selects the level (e.g., PT) for re-analysis and is given the results in real time. The user can then iterate between high level and detail. It will be appreciated that the invention is not restricted to drug and reaction dimensions for proportional analysis. All pairs of the dimensions of the analytical engine (for example, reaction and outcomes) can be analyzed. Even within the cases of a single drug, the reactions and concomitant drugs could be proportionally analyzed.

Figures 18, 19:
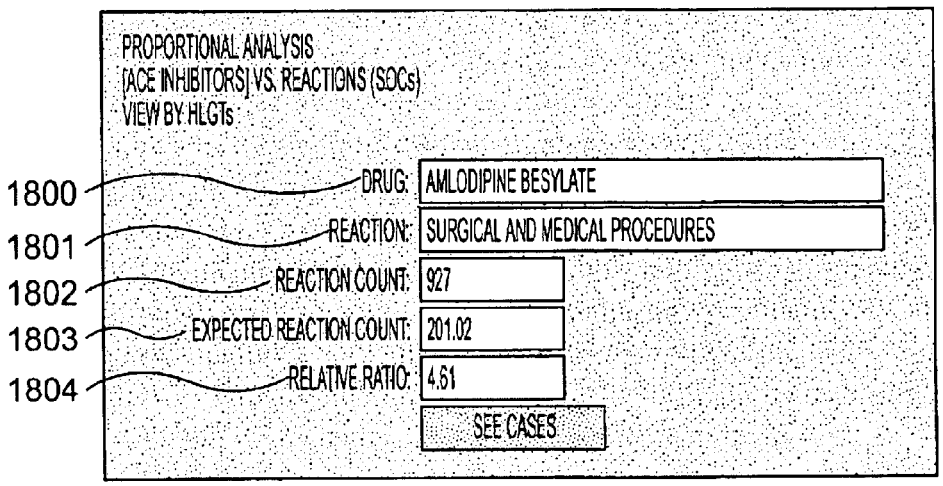
FIG. 18 is a representation of a proportional analysis results screen of the present invention.
FIG. 19 is a depiction of a tabular version of a proportional analysis screen of the present invention.

In addition to the graphic display, the proportional analyzer also shows these data in a tabular form. FIG. 19 is the tabular presentation of the proportional analysis results. In this table, the location of the drug (field 1901) and its reaction (field 1900) in the matrix are indicated by numbers for row and column, row indicating the reaction and column signifying the drug of interest. The remaining three columns in the table preferably indicate the reaction count (field 1902)(with a hyperlink to the cases themselves), the expected reaction count (field 1903), and the Relative Ratio (field 1904). The entries are ranked in descending order, with the highest ratios listed first. The columns can preferably be sorted by clicking on their headings.

As in all tables, from the selector to the correlator, numbers are hyperlinked to the case-list. In the proportional analysis engine, all HLTs are available.

Figure 20:
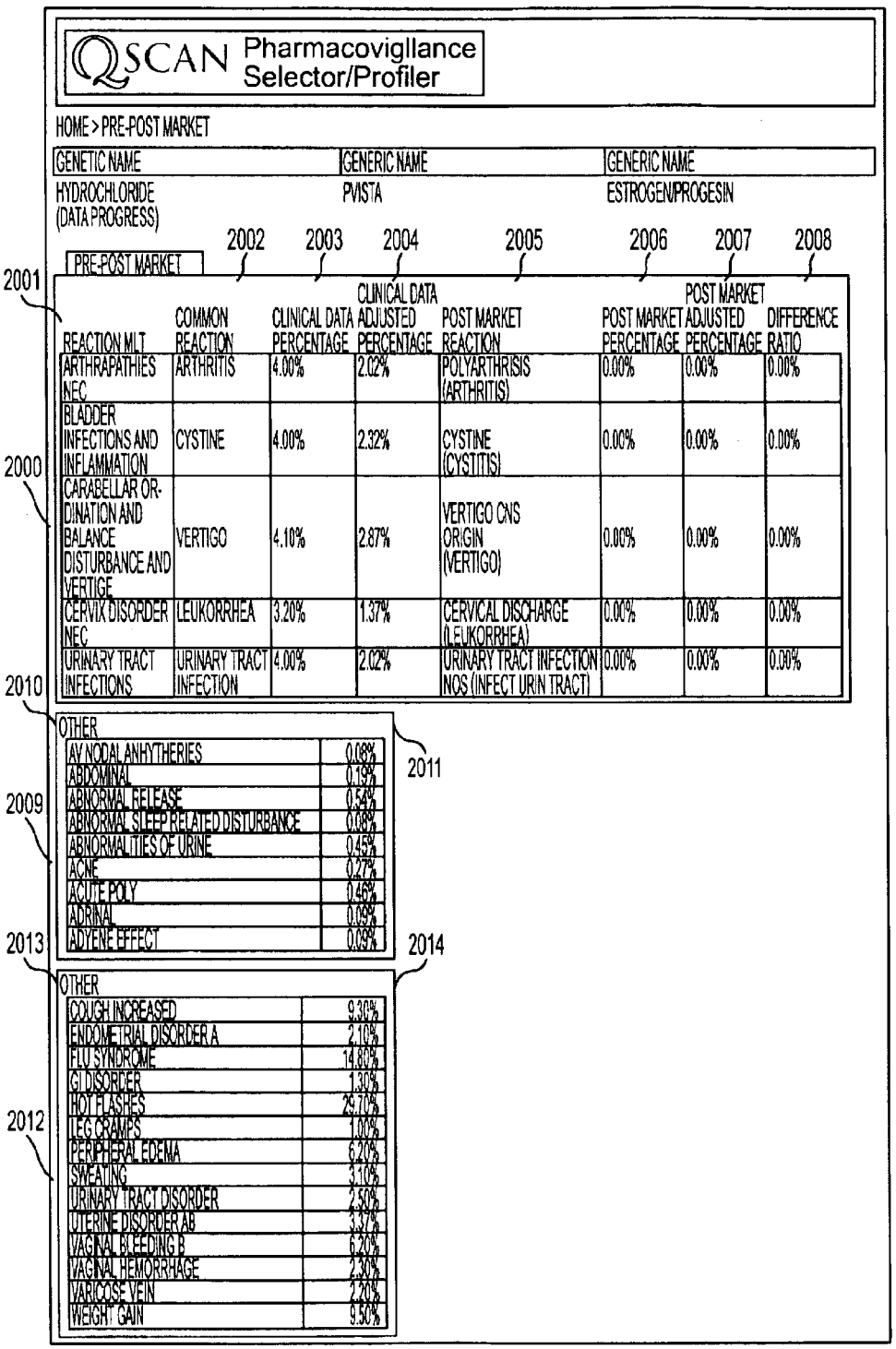
FIG. 20 is an illustration of a comparator screen of the present invention.

The comparator or differencing engine screen in the preferred offering offers three sets of analyzed data: Pre/Post Market data, Other Post-Market Reaction, and Other Clinical Trial Reaction. An exemplary comparator screen is provided in FIG. 20. The Pre/Post Market data is preferably organized into a series of columns in a first table (field 2000), providing the information, including Reaction HLT (field 2001); Clinical Trial Reaction (field 2002); Clinical Trial Percentage (field 2003), Clinical Trial Adjusted Percentage (field 2004); Post Market Reaction (field 2005); Post Market Percentage (field 2006); Post Market Adjusted Percentage (field 2007); and Difference Ratio (field 2008). The adjusted percentages account for proportions of those reactions that are common in both pre- and post-market reporting. The second table (field 2009)lists Other Post-Market Reaction (field 2010)and each reaction's Post-Market Percentage (field 2011). This information represents data available in the integrated public database. The third table (field 2012)provides Other Clinical Trial Reaction (field 2013)and each reaction's Clinical Trial Percentage (field 2014). This information indicates whether this reaction was mentioned on the manufacturer's package insert.

The comparator engine of the present invention is a differencing engine that is applied to measuring one drug's reactions, both pre- and post-market. This engine is essentially a "proportion of proportions" and is preferably limited to situations where: labeled adverse effect data can be quantified, terms can be mapped to MedDRA, and a useful number of reports are available for reactions, both pre- and post-market. The comparator can compare any two sets of cases for any two dimensions.

In viewing the results of the system and method of the present invention, when a box on a table or in a matrix or a hyperlink is selected, the case listing is generated. When a user clicks on any of the numbers, he/she is provided with a listing of each of the cases corresponding to that link. An exemplary Case List is provided in FIG. 21. For each case, various information is provided, including case ID (field 2100), gender (field 2101), Manufacturer Control Code (field 2102), FDA Report Receipt Date (field 2103), Age (field 2104), Drugs (field 2105), Reactions (field 2106), Seriousness (field 2107)(Y/N or normal outcome (optional)). These columns can be sorted by clicking on their headings. If a user selects a summary view, a profile of the cases in the case list is then calculated and displayed. Additionally, if a user wishes to learn the details of a specific case, he/she can click on the case ID number of any specific case on the correlation details screen.

This Case Details screen provides detailed information on each specific case. In addition to standard information such as the patient's case ID, gender, and age, it also includes Reactions (including detailed information in the As Reported, Preferred Term, High Level Term, and High Level Group Term categories); Concomitant Drugs (each listed by Name, Dose, Route, and Suspect Status); Outcomes; Manufacturer Control Code; Manufacturer Date; Adverse Event Date; Report Type; Report Source; Case Source; and Narrative, if any. As will be appreciated, additional details can be provided. If these details are structured, all features of the invention are expandable to that dimension. If the information is unstructured, the invention can extract and structure the data using the dictionary and thesaurus facilities.

Various preferred embodiments of the invention have been described in fulfillment of the various objects of the invention. It should be recognized that these embodiments are merely illustrative of the principles of the invention.

Numerous modifications and adaptations thereof will be readily apparent to those skilled in the art without departing from the spirit and scope of the present invention.

What is claimed is:

1. A computer-implemented method for assessing and analyzing the risks of adverse effects resulting from the use of at least one drug of interest, comprising:

storing data regarding the risks of adverse effects from the use of at least one drug of interest in one or more servers linked to the Internet;

updating such data regarding the risks with additional information pertinent to the risks of adverse effects from the use of the at least one drug of interest;

permitting at least one remote user to access such data through the World Wide Web upon proper authentication;

permitting the at least one user to identify the at least one drug of interest;

permitting the at least one remote user to select data stored in the one or more servers relevant to the safety of using the at least one drug of interest;

permitting the at least one remote user to analyze safety issues resulting from the use of the at least one drug of interest; and permitting the at least one remote user to display such data and analysis, wherein the step of permitting the at least one remote user to analyze comprises associating respective hyperlinks with a plurality of portions of such data and analysis, the plurality of hyperlinks respectively corresponding to places in an up and down hierarchy and allowing analytical drill down by selectively selecting successive hyperlinks, a last one of the hyperlinks in the up and down hierarchy linking to a previously-stored case describing adverse effects resulting from the use of the at least one drug of interest.

2. The computer-implemented method for assessing and analyzing the risks of adverse effects resulting from the use of at least one drug of interest according to claim 1, wherein the analysis of the at least one remote user is performed by at least one data mining engine.

3. The computer-implemented method for assessing and analyzing the risks of adverse effects resulting from the use of at least one drug of interest according to claim 2, wherein the at least one data mining engine is a proportional analysis engine to assess deviations in a set of the reactions to the at least one drug of interest.

4. The computer-implemented method for assessing and analyzing the risks of adverse effects resulting from the use of at least one drug of interest according to claim 2, wherein the at least one data mining engine is a comparator to measure the reactions to the at least one drug of interest against a user-defined backdrop.

5. The computer-implemented method of assessing and analyzing the risks of adverse effects resulting from the use of at least one drug of interest according to claim 2, wherein the at least one data mining engine is a correlator to look for correlated signal characteristics among drug, reaction, and demographic information.

6. The computer-implemented method for assessing and analyzing the risks of adverse effects resulting from the use of at least one drug of interest according to claim 2, wherein the data mining engine is at least two members of the group consisting of a proportional analysis engine, a comparator, and a correlator.

7. The computer-implemented method for assessing and analyzing the risks of adverse effects resulting from the use of at least one drug of interest according to claim 1, wherein the at least one drug of interest is assessed in combination with other drugs, foodstuffs, beverages, nutrients, vitamins, toxins, chemicals, hormones, and supplements.

8. A computer implemented method for assessing and analyzing the risks of adverse effects resulting from the use of at least one substance of interest, comprising:

storing data regarding the risks of adverse effects from the use of at least one substance of interest in one or more servers linked to the Internet;

updating such data regarding the risks with additional information pertinent to the risks of adverse effects from the use of the at least one substance of interest;

permitting at least one remote user to access such data through the World Wide Web upon proper authentication;

permitting the at least one user to identify the at least one substance of interest;

permitting the at least one remote user to select data stored in the one or more servers relevant to the safety of using the at least one substance of interest;

permitting the at least one remote user to analyze safety issues resulting from the use of the at least one substance of interest; and permitting the at least one remote user to display such data and analysis, wherein the step of permitting the at least one remote user to analyze comprises associating respective hyperlinks with a plurality of portions of such data and analysis, the plurality of hyperlinks respectively corresponding to places in an up and down hierarchy and allowing analytical drill down by selectively selecting successive hyperlinks, a last one of the hyperlinks in the up and down hierarchy linking to a previously-stored case describing adverse effects resulting from the use of the at least one substance of interest.

9. The computer-implemented method for assessing and analyzing the risks of adverse effects resulting from the use of at least one substance of interest according to claim 8, wherein the analysis of the at least one remote user is performed by at least one data mining engine.

10. The computer-implemented method for assessing and analyzing the risks of adverse effects resulting from the use of at least one substance of interest according to claim 9, wherein the at least one data mining engine is a proportional analysis engine to assess deviations in a set of the reactions to the at least one substance of interest.

11. The computer-implemented method for assessing and analyzing the risks of adverse effects resulting from the use of at least one substance of interest according to claim 9, wherein the at least one data mining engine is a comparator to measure the reactions to the at least one substance of interest against a user-defined backdrop.

12. The computer-implemented method of assessing and analyzing the risks of adverse effects resulting from the use of at least one substance of interest according to claim 9, wherein the at least one data mining engine is a correlator to look for correlated signal characteristics among drug, reaction, and demographic information.

13. The computer-implemented method for assessing and analyzing the risks of adverse effects resulting from the use of at least one substance of interest according to claim 9, wherein the data mining engine is at least two members of the group consisting of a proportional analysis engine, a comparator, and a correlator.

14. The computer-implemented method for assessing and analyzing the risks of adverse effects resulting from the use of at least one substance of interest according to 8, wherein the at least one substance of interest is assessed in combination with other drugs, foodstuffs, beverages, nutrients, vitamins, toxins, chemicals, hormones, and supplements.

15. The computer-implemented method for assessing and analyzing the risks of adverse effects resulting from the use of at least one drug of interest according to claim 1, wherein the step of permitting the at least one user to analyze further comprises finding signals consistent with at least one of anomalies in a random population, a change against a known background and a coherent target in a noise background.

16. The computer-implemented method for assessing and analyzing the risks of adverse effects resulting from the use of at least one substance of interest according to claim 8, wherein the step of permitting the at least one user to analyze further comprises finding signals consistent with at least one of anomalies in a random population, a change against a known background and a coherent target in a noise background.

* * * * *